US011408011B2

(12) United States Patent
Blumwald et al.

(10) Patent No.: US 11,408,011 B2
(45) Date of Patent: Aug. 9, 2022

(54) PLANT TOLERANCE TO STRESS THROUGH THE CONTROL OF CHLOROPLAST STABILITY

(71) Applicant: The Regents of the University of California, Oakland, CA (US)

(72) Inventors: Eduardo Blumwald, Davis, CA (US); Songhu Wang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 300 days.

(21) Appl. No.: 16/417,179

(22) Filed: May 20, 2019

(65) Prior Publication Data

US 2019/0309318 A1  Oct. 10, 2019

Related U.S. Application Data

(63) Continuation of application No. 15/030,355, filed as application No. PCT/US2014/062900 on Oct. 29, 2014, now abandoned.

(60) Provisional application No. 61/897,006, filed on Oct. 29, 2013.

(51) Int. Cl.
*C12N 15/82* (2006.01)
*A01H 1/06* (2006.01)

(52) U.S. Cl.
CPC ........... *C12N 15/8273* (2013.01); *A01H 1/06* (2013.01); *C12N 15/8205* (2013.01); *C12N 15/8218* (2013.01); *C12N 15/8237* (2013.01)

(58) Field of Classification Search
None
See application file for complete search history.

(56) References Cited

U.S. PATENT DOCUMENTS

2004/0031072 A1   2/2004  La Rosa et al.
2004/0123343 A1*  6/2004  La Rosa .............. C07K 14/415
                                                        800/278

FOREIGN PATENT DOCUMENTS

WO      2005/055704 A2    6/2005

OTHER PUBLICATIONS

Till et al. (BMC plant biology 7.1 (2007): 1-12). (Year: 2007).*
McCallum et al. ( Nature biotechnology 18.4 (2000): 455). (Year: 2000).*
Ren et al. (Journal of Integrative Plant Biology 2010, 52 (5): 496-504). (Year: 2010).*
Tian et al. (Biologia plantarum 56.3 (2012): 509-515). (Year: 2012).*
GenBank Accession NM 179732 (1999). (Year: 1999).*
Jang et al., "Insights into Alternanthera Mosaic VirusTGB3 Functions: Interactions with Nicotiana Benthamiana PsbO Correlate with Chloroplast Vesticulation and Veinal Necrosis Caused by TGB3 Over-Expression," *Plant Science*, Jan. 1, 2013, vol. 4, p. 1-15.
SEQ ID No. 195455 from US 2004/0031072 A1, Feb. 12, 2004.
Wang et al., "Stress-Induced Chloroplast Degradation in *Arabidopsis* is Regulated via a Process Independent of Atophagy and Senescence-Associated Vacuoles," *Plant Cell*, Dec. 23, 2014, p. 1-14.
International Search Report in PCT/US2014/062900 dated Feb. 11, 2015.
GenBank Accession No. NM_179732; Sep. 16, 2003.
McCallum et al.; *Nature Biotechnology* 18.4; 2000; p. 455.
Ren, G. et al.; "Reverse Genetic Identification of CRN1 and its Distinctive Role in Chlorophyll Degradation in *Arabidopsis*"; *Journal of Integrative Plant Biology*; vol. 52, No. 5; 2010; pp. 496-504.
Tian, F.X. et al.; "Improved drought resistance in a wheat stay-green mutant tasg1 under field conditions"; *Biologia Plantarum*; vol. 56, No. 3; 2012; pp. 509-515.
GenBank Accession AEC07727; Feb. 28, 2011; 2 pages.
Miao, J. et al.; "Targeted mutagenesis in rice using CRISPR-Cas system"; *Cell Research*; vol. 23, No. 10; Oct. 2013; pp. 1233-1236.
Zhang, F. et al.; "Histone Deacetylases SRT1 and SRT2 Interact with ENAP1 to Mediate Ethylene-Induced Transcriptional Repression"; *The Plant Cell*; Jan. 3, 2018; tpc.17.00671; 37 pages.

* cited by examiner

*Primary Examiner* — Charles Logsdon
(74) *Attorney, Agent, or Firm* — Kilpatrick Townsend & Stockton LLP

(57) ABSTRACT

The chloroplast vesiculation (CV) gene encodes a protein associated with stress-induced chloroplast degradation. Inhibiting expression or activity of the protein inhibits or delays stress-induced chloroplast degradation and confers tolerance to a variety of stress conditions. Alternatively, enhancing CV expression or activity promotes chloroplast degradation and enhances nutrient assimilation in desired sink tissues, such as young leaves, fruit, or seeds.

5 Claims, 3 Drawing Sheets

Specification includes a Sequence Listing.

A

B

A

B

SEQUENCE LISTING

<160> NUMBER OF SEQ ID NOS: 48

<210> SEQ ID NO 1
<211> LENGTH: 459
<212> TYPE: DNA
<213> ORGANISM: Arabidopsis thaliana
<220> FEATURE:
<223> OTHER INFORMATION: chloroplast vesiculation (CV) AT2G25625

<400> SEQUENCE: 1

```
atggcaggga gaataagctg ctgtctaaat cttcctcccc tagattcaaa ttctgcacaa    60
tcattagctt cactgctcaa gacaacgtca aagatctctt gtaggagaac agaaaatgag   120
acagagccac ggaaaaacaa gtgttctttt gtcttggggg tggcggcaac tgtcgtaatc   180
ggcgggattc agatcaatga tgttgcatca gtggaagctg cggttgtgaa atcgccggta   240
gaagagatgg ctgcgggtgt ggtgccgccg cggaggtgga gtgacaagag gacgtgtccg   300
ccttggcttg agaactcgct agagaccatc gtaccggaga tcttcctcg tccgtctgct   360 catcgacgtt tggagttagc cggattagct aagggtgatg caccgccggt cggtgtggtg   420
```

```
atgacacgtg tcaacagggg tggttgtttc tccgtgtaa                    459
```

<210> SEQ ID NO 2
<211> LENGTH: 152
<212> TYPE: PRT
<213> ORGANISM: Arabidopsis thaliana
<220> FEATURE:
<223> OTHER INFORMATION: chloroplast vesiculation (CV) AT2G25625

<400> SEQUENCE: 2

```
Met Ala Gly Arg Ile Ser Cys Cys Leu Asn Leu Pro Pro Leu Asp Ser
1               5                   10                  15

Asn Ser Ala Gln Ser Leu Ala Ser Leu Leu Lys Thr Thr Ser Lys Ile
            20                  25                  30

Ser Cys Arg Arg Thr Glu Asn Glu Thr Glu Pro Arg Lys Asn Lys Cys
        35                  40                  45

Ser Phe Val Leu Gly Val Ala Ala Thr Val Val Ile Gly Gly Ile Gln
    50                  55                  60

Ile Asn Asp Val Ala Ser Val Glu Ala Ala Val Val Lys Ser Pro Val
65                  70                  75                  80

Glu Glu Met Ala Ala Gly Val Val Pro Pro Arg Arg Trp Ser Asp Lys
                85                  90                  95

Arg Thr Cys Pro Pro Trp Leu Glu Asn Ser Leu Glu Thr Ile Val Pro
            100                 105                 110

Glu Asn Leu Pro Arg Pro Ser Ala His Arg Arg Leu Glu Leu Ala Gly
        115                 120                 125

Leu Ala Lys Gly Asp Ala Pro Pro Val Gly Val Met Thr Arg Val
    130                 135                 140

Asn Arg Gly Gly Cys Phe Ser Val
145                 150
```

<210> SEQ ID NO 3
<211> LENGTH: 465
<212> TYPE: DNA
<213> ORGANISM: Brachypodium distachyon
<220> FEATURE:
<223> OTHER INFORMATION: chloroplast vesiculation (CV) BD2G15690

<400> SEQUENCE: 3

```
atgccggtct cctccgccat cagctgctgc cagcagctca gacctccggg tccacctccg    60
gcgccgagag aagaaggcag cagcagcagt agtcgtatcc cgctgtcgcg gcgcagggcg   120
tgctttctcg cggcggcggc ggcgtgcgtg gtggccgtgg cggcgggagg ggccggagaa   180
gcagcggcga tggcgcgggg cgcgccgcac gagcacgagg cggcggcggc ggtgcgcgtg   240
caggctgggg cggcggcgag gtggagcgag cgcaggcagt gcccgccgtg gcgggcgaat   300
tcgctggaga acgtagtgcc ggagaacctg ccgcgcccgt cggcgcggcg gaggtacaac   360
ggcgtcgggg agagggatcc cgcgccggcg ccagccgcgt cgcctgaggc cgtgctcccg   420
ttcctggcgc tgcgctccgg cggcatgggc tgcttctctc tctaa              465
```

<210> SEQ ID NO 4
<211> LENGTH: 154
<212> TYPE: PRT
<213> ORGANISM: Brachypodium distachyon
<220> FEATURE:
<223> OTHER INFORMATION: chloroplast vesiculation (CV) BD2G15690

<400> SEQUENCE: 4

Met Pro Val Ser Ser Ala Ile Ser Cys Cys Gln Gln Leu Arg Pro Pro

```
                1               5              10              15
            Gly Pro Pro Pro Ala Pro Arg Glu Glu Gly Ser Ser Ser Ser Ser Arg
                               20                  25                  30

Ile Pro Leu Ser Arg Arg Arg Ala Cys Phe Leu Ala Ala Ala Ala Ala
                               35                  40                  45

Cys Val Val Ala Val Ala Ala Gly Gly Ala Gly Glu Ala Ala Ala Met
                50                              55                  60

Ala Arg Gly Ala Pro His Glu His Glu Ala Ala Ala Val Arg Val
            65                  70                  75                  80

Gln Ala Gly Ala Ala Ala Arg Trp Ser Glu Arg Arg Gln Cys Pro Pro
                                85                  90                  95

Trp Arg Ala Asn Ser Leu Glu Asn Val Val Pro Glu Asn Leu Pro Arg
                               100                 105                 110

Pro Ser Ala Arg Arg Tyr Asn Gly Val Gly Glu Arg Asp Pro Ala
                               115                 120                 125

Pro Ala Pro Ala Ala Ser Pro Glu Ala Val Leu Pro Phe Leu Ala Leu
                           130                 135                 140

Arg Ser Gly Gly Met Gly Cys Phe Ser Leu
            145                 150

<210> SEQ ID NO 5
<211> LENGTH: 519
<212> TYPE: DNA
<213> ORGANISM: Carica papaya
<220> FEATURE:
<223> OTHER INFORMATION: chloroplast vesiculation (CV) CP00603G00010

<400> SEQUENCE: 5
atggatatgg aggatagatt acagaagaaa tgtggagatt tgagcctgat ctactccgga      60
agacatgaga gaggtttttg ggcgattgac acgaggattc ctggtttccg gcgaatgctc     120
aggaacaatg tgaagaggag tcgtctggtt aaacgaaacg gtagagaggg agagagtgaa     180
gatgatggcg atgagagtaa gttgctgcct aaaccttcct cctcgagaaa aaccttcact     240
ccatctccct cctcctgcca acacgttttc tcaattacct tcaaggaaaa aggaagaatg     300
ttggaggaag aagagtgcgg tggcgatggc gtgcttggta attggattga tacaggtggc     360
aaatggagcg aaaagagaat gtgtccgcca tggcatgcta actcccttga accgtcgtg     420 ccggagaatc tccctcggcc atctgctcgt cggagatggc agcttgttgc tttcaccccc     480
aaccttcgtc agcccccacc cacatgtttc tctttgtga                           519

<210> SEQ ID NO 6
<211> LENGTH: 172
<212> TYPE: PRT
<213> ORGANISM: Carica papaya
<220> FEATURE:
<223> OTHER INFORMATION: chloroplast vesiculation (CV) CP00603G00010

<400> SEQUENCE: 6

Met Asp Met Glu Asp Arg Leu Gln Lys Lys Cys Gly Asp Leu Ser Leu
            1               5                  10                  15

Ile Tyr Ser Gly Arg His Glu Arg Gly Phe Trp Ala Ile Asp Thr Arg
                            20                  25                  30

Ile Pro Gly Phe Arg Arg Met Leu Arg Asn Asn Val Lys Arg Ser Arg
                            35                  40                  45

Leu Val Lys Arg Asn Gly Arg Glu Gly Glu Ser Glu Asp Asp Gly Asp
                50                              55                  60
```

| | | | | | | | | | | | | | | |
|---|---|---|---|---|---|---|---|---|---|---|---|---|---|---|
|Glu|Ser|Lys|Leu|Leu|Pro|Lys|Pro|Ser|Ser|Ser|Arg|Lys|Thr|Phe|Thr|
|65| | | |70| | | |75| | | |80| | | |

Pro Ser Pro Ser Ser Cys Gln His Val Phe Ser Ile Thr Phe Lys Glu
               85                 90               95

Lys Gly Arg Met Leu Glu Glu Glu Cys Gly Gly Asp Gly Val Leu
           100                 105                110

Gly Asn Trp Ile Asp Thr Gly Gly Lys Trp Ser Glu Lys Arg Met Cys
           115                 120                125

Pro Pro Trp His Ala Asn Ser Leu Glu Thr Val Val Pro Glu Asn Leu
     130                 135                140

Pro Arg Pro Ser Ala Arg Arg Arg Trp Gln Leu Val Ala Phe Thr Pro
145             150                 155                160

Asn Leu Arg Gln Pro Pro Thr Cys Phe Ser Leu
           165                 170

<210> SEQ ID NO 7
<211> LENGTH: 447
<212> TYPE: DNA
<213> ORGANISM: Fragaria vesca
<220> FEATURE:
<223> OTHER INFORMATION: chloroplast vesiculation (CV) FV2G40830

<400> SEQUENCE: 7

```
atggccatga caagcttcag ctgcagcctt aaccagctgc cgcctccagc tcaaagctta      60
ggcccttctt cccctcaaa gacgaatcaa gtacaacttg catggaacaa aagcgaggga     120
ggatcatgga gtagcagatg tgttgtgggc atggcttgtg ttatggttgg gttggagatg     180
ggtggtttgg tgagtggcca aagccatgaa gctattgcta aaggtatgcc gccgttggtg     240
atggagtcaa gtgagaaagt tgcaaagtgg agtgacaaga gaatgtgccc aaagtggaga     300
gccaatgagc tggagaccat tgtgccggag aatcttccga ggccgtcggc tcaccggaga     360
tgggaaatcg tcgggtttaa tactagggat gctccggcgg ttaagacggt agctaggagg     420
agtagcggtg gttgcttttc tatgtaa                                        447
```

<210> SEQ ID NO 8
<211> LENGTH: 148
<212> TYPE: PRT
<213> ORGANISM: Fragaria vesca
<220> FEATURE:
<223> OTHER INFORMATION: chloroplast vesiculation (CV) FV2G40830

<400> SEQUENCE: 8

Met Ala Met Thr Ser Phe Ser Cys Ser Leu Asn Gln Leu Pro Pro Pro
1               5                 10                15

Ala Gln Ser Leu Gly Pro Ser Ser Pro Ser Lys Thr Asn Gln Val Gln
           20                 25                30

Leu Ala Trp Asn Lys Ser Glu Gly Gly Ser Trp Ser Ser Arg Cys Val
           35                 40                45

Val Gly Met Ala Cys Val Met Val Gly Leu Glu Met Gly Gly Leu Val
           50                 55                60

Ser Gly Gln Ser His Glu Ala Ile Ala Lys Gly Met Pro Pro Leu Val
65              70                 75                80

Met Glu Ser Ser Glu Lys Val Ala Lys Trp Ser Asp Lys Arg Met Cys
           85                 90                95

Pro Lys Trp Arg Ala Asn Glu Leu Glu Thr Ile Val Pro Glu Asn Leu
           100                 105                110

Pro Arg Pro Ser Ala His Arg Arg Trp Glu Ile Val Gly Phe Asn Thr

```
                115                 120                 125
Arg Asp Ala Pro Ala Val Lys Thr Val Ala Arg Arg Ser Ser Gly Gly
    130                 135                 140

Cys Phe Ser Met
145

<210> SEQ ID NO 9
<211> LENGTH: 384
<212> TYPE: DNA
<213> ORGANISM: Glycine max
<220> FEATURE:
<223> OTHER INFORMATION: chloroplast vesiculation (CV) GM04G07440
      (Glycine max-1)

<400> SEQUENCE: 9
atgaggacca cttgcttact aagccttccc cctcttactt caaaccaacc ctccaacgct      60
tctttcaacc ccgcaaagcc acctcaactt tcatcgcaat gcgttatgat gggagtggca    120
tccataattg actagaaat gtgcaattta gtggcactgg cccacgaagc aattgaaatc     180
acaactatgc caattggtaa ccaagtaaaa agaacgtgct caccttggca aggcaactcg    240
ctcgaaacca tcatgccgga gaaccttccc cggccgtcgg cacggcggcg atacgaggct    300
gttcgttcct ccaccaagac tgtgccaccg tcctcagccc cgatcatagt ccaaagcaac    360
aagggcagct gcttctccat gtga                                           384

<210> SEQ ID NO 10
<211> LENGTH: 127
<212> TYPE: PRT
<213> ORGANISM: Glycine max
<220> FEATURE:
<223> OTHER INFORMATION: chloroplast vesiculation (CV) GM04G07440
      (Glycine max-1)

<400> SEQUENCE: 10

Met Arg Thr Thr Cys Leu Leu Ser Leu Pro Pro Leu Thr Ser Asn Gln
1               5                   10                  15

Pro Ser Asn Ala Ser Phe Asn Pro Ala Lys Pro Pro Gln Leu Ser Ser
            20                  25                  30

Gln Cys Val Met Met Gly Val Ala Ser Ile Ile Gly Leu Glu Met Cys
        35                  40                  45

Asn Leu Val Ala Leu Ala His Glu Ala Ile Glu Ile Thr Thr Met Pro
    50                  55                  60

Ile Gly Asn Gln Val Lys Arg Thr Cys Ser Pro Trp Gln Gly Asn Ser
65                  70                  75                  80

Leu Glu Thr Ile Met Pro Glu Asn Leu Pro Arg Pro Ser Ala Arg Arg
                85                  90                  95

Arg Tyr Glu Ala Val Arg Ser Ser Thr Lys Thr Val Pro Pro Ser Ser
            100                 105                 110

Ala Pro Ile Ile Val Gln Ser Asn Lys Gly Ser Cys Phe Ser Met
        115                 120                 125

<210> SEQ ID NO 11
<211> LENGTH: 441
<212> TYPE: DNA
<213> ORGANISM: Glycine max
<220> FEATURE:
<223> OTHER INFORMATION: chloroplast vesiculation (CV) GM06G07560
      (Glycine max-2)

<400> SEQUENCE: 11
```

```
atgaggacca gttgcttcct aagccttccc ccttttactt caaaccaacc ttccattccc    60
ccaaaacatc ctcaactttc atcggtgaag aacgaagcat gttggaagag caatgcgtt    120 gtgatgggag tggcatccat tattggacta gaaatgtgca attcagtggc aatggcccac   180
gaagcaattg aaatcaagac catgccattt agtaaccaag tagtatcaaa tagcaattct   240
tacggtggcg ccaaatggag cgagaaaaga atgtgcccac cttggcaagg caattcgctc   300
gaaacgatcg tgccggagaa tcttccccgg ccgtcggcac ggcggagata cgaggctgtt   360
cgttcctcct ccaagactgc cgccgcgctc tccgccccga tcatagtcca aagcaacaag   420
ggcagttgct ctccatgtg a                                              441
```

```
<210> SEQ ID NO 12
<211> LENGTH: 146
<212> TYPE: PRT
<213> ORGANISM: Glycine max
<220> FEATURE:
<223> OTHER INFORMATION: chloroplast vesiculation (CV) GM06G07560
      (Glycine max-2)

<400> SEQUENCE: 12
```

Met Arg Thr Ser Cys Phe Leu Ser Leu Pro Pro Phe Thr Ser Asn Gln
1               5                   10                  15

Pro Ser Ile Pro Pro Lys His Pro Gln Leu Ser Ser Val Lys Asn Glu
            20                  25                  30

Ala Cys Trp Lys Arg Gln Cys Val Val Met Gly Val Ala Ser Ile Ile
        35                  40                  45

Gly Leu Glu Met Cys Asn Ser Val Ala Met Ala His Glu Ala Ile Glu
    50                  55                  60

Ile Lys Thr Met Pro Phe Ser Asn Gln Val Val Ser Asn Ser Asn Ser
65                  70                  75                  80

Tyr Gly Gly Ala Lys Trp Ser Glu Lys Arg Met Cys Pro Pro Trp Gln
                85                  90                  95

Gly Asn Ser Leu Glu Thr Ile Val Pro Glu Asn Leu Pro Arg Pro Ser
            100                 105                 110

Ala Arg Arg Arg Tyr Glu Ala Val Arg Ser Ser Ser Lys Thr Ala Pro
        115                 120                 125

Pro Leu Ser Ala Pro Ile Ile Val Gln Ser Asn Lys Gly Ser Cys Phe
    130                 135                 140

Ser Met
145

```
<210> SEQ ID NO 13
<211> LENGTH: 189
<212> TYPE: DNA
<213> ORGANISM: Lotus japonicus
<220> FEATURE:
<223> OTHER INFORMATION: chloroplast vesiculation (CV) LJ0G026030

<400> SEQUENCE: 13
gccaaatgga gccagaaaag ggcgtgtcct ccttggcgag gtaacgcttt ggaaaccatc    60
gtgccggaga atcttccgcg gccagcggcg cggcggagat acgaggctgt tcggtcaacc   120
tccaagacgg cgccgccgct ctctgaagcc ttcaaaatta aatccaacag ttatagttgc   180
ttctccatg                                                          189
```

```
<210> SEQ ID NO 14
<211> LENGTH: 63
<212> TYPE: PRT
```

<213> ORGANISM: Lotus japonicus
<220> FEATURE:
<223> OTHER INFORMATION: chloroplast vesiculation (CV) LJ0G026030

<400> SEQUENCE: 14

```
Ala Lys Trp Ser Gln Lys Arg Ala Cys Pro Pro Trp Arg Gly Asn Ala
1               5                   10                  15

Leu Glu Thr Ile Val Pro Glu Asn Leu Pro Arg Pro Ala Ala Arg Arg
            20                  25                  30

Arg Tyr Glu Ala Val Arg Ser Thr Ser Lys Thr Ala Pro Pro Leu Ser
        35                  40                  45

Glu Ala Phe Lys Ile Lys Ser Asn Ser Tyr Ser Cys Phe Ser Met
    50                  55                  60
```

<210> SEQ ID NO 15
<211> LENGTH: 603
<212> TYPE: DNA
<213> ORGANISM: Malus domestica
<220> FEATURE:
<223> OTHER INFORMATION: chloroplast vesiculation (CV) MD00G178660
      (Malus domestica-1)

<400> SEQUENCE: 15

| | | |
|---|---|---|
| atggcttgtt ttagagggtc accattgagg tctttgtcat ctcttttaac cttatgcaac | 60 |
| caaacccacc ttcctctttt gatatatacg atccctctcc ttctgtcatt gcttaaattc | 120 |
| agagagaaca gagagagaga gagagagaaa gggatgactg ttacaaactt caattgctgc | 180 |
| ctcaatccgc caccttcaaa tcaaaaccat ggttcaagcc cttctttgcc cttaaagaaa | 240 |
| aaccaagcac ttgcatggaa caaatatgct catggatcat ggactaatcg atgcgttttta | 300 |
| ggtatgagtt gcgcaattgg attggaaatg gaaccctag taagcaacca aaactatgag | 360 |
| gccattgcta tgctatgcc ttcgccgttg gaaatagaaa catatagtga tcagagggtt | 420 |
| gaaaaatgga gtgacaaaag aatatgccca caatggagcc ctaattcaca agagaccatt | 480 |
| gtgcctgaaa atctcccaag atcatctgct caaaggagat gggaaacagt tggttttct | 540 |
| aacgaggatg ctccggcggt tcaaatggta gttagaaaag gtggcaactg ctttgctatg | 600 |
| tag | 603 |

<210> SEQ ID NO 16
<211> LENGTH: 200
<212> TYPE: PRT
<213> ORGANISM: Malus domestica
<220> FEATURE:
<223> OTHER INFORMATION: chloroplast vesiculation (CV) MD00G178660
      (Malus domestica-1)

<400> SEQUENCE: 16

```
Met Ala Cys Phe Arg Gly Ser Pro Leu Arg Ser Leu Ser Ser Leu Leu
1               5                   10                  15

Thr Leu Cys Asn Gln Thr His Leu Pro Leu Leu Ile Tyr Thr Ile Pro
            20                  25                  30

Leu Leu Leu Ser Leu Leu Lys Phe Arg Glu Asn Arg Glu Arg Glu Arg
        35                  40                  45

Glu Lys Gly Met Thr Val Thr Asn Phe Asn Cys Cys Leu Asn Pro Pro
    50                  55                  60

Pro Ser Asn Gln Asn His Gly Ser Ser Pro Ser Leu Pro Leu Lys Lys
65                  70                  75                  80

Asn Gln Ala Leu Ala Trp Asn Lys Tyr Ala His Gly Ser Trp Thr Asn
                85                  90                  95
```

Arg Cys Val Leu Gly Met Ser Cys Ala Ile Gly Leu Glu Met Gly Thr
            100                 105                 110

Leu Val Ser Asn Gln Asn Tyr Glu Ala Ile Ala Asn Ala Met Pro Ser
        115                 120                 125

Pro Leu Glu Ile Glu Thr Tyr Ser Asp Gln Arg Val Glu Lys Trp Ser
    130                 135                 140

Asp Lys Arg Ile Cys Pro Gln Trp Ser Pro Asn Ser Gln Glu Thr Ile
145                 150                 155                 160

Val Pro Glu Asn Leu Pro Arg Ser Ser Ala Gln Arg Arg Trp Glu Thr
                165                 170                 175

Val Gly Phe Ser Asn Glu Asp Ala Pro Ala Val Gln Met Val Val Arg
            180                 185                 190

Lys Gly Gly Asn Cys Phe Ala Met
        195                 200

<210> SEQ ID NO 17
<211> LENGTH: 453
<212> TYPE: DNA
<213> ORGANISM: Malus domestica
<220> FEATURE:
<223> OTHER INFORMATION: chloroplast vesiculation (CV) MD00G406410
      (Malus domestica-2)

<400> SEQUENCE: 17
atgactgtta caaacttcaa ttgctgcctc aatccgccac cttcaaatca aaaccatggt      60
tcaagccctt ctttgccctt aaagcaaaac caagcacttg catggaacaa atatgctcat     120
ggatcatgga ctaatcgatg cgttttaggt atgagttgca tcgcaattgg atatgaaatg     180
ggaaccctag taagcaacca aaactatgag gccattgcta atgctatgcc ttcgccgttg     240
gaaatagaaa catcaagtga tcagagggtt gcaaaatgga gtgacaaaag aatgtgccca     300
caatggagcc ctaattcgct agagaccatt gtgcctgaaa atcttccaag accatctgct     360
caaatgagat gggaaaccgt tggttttct gacaaggatg ctccggtggt tcaaatggta     420
gttagaaaag gtggcagctg ctttgctatg tag                                  453

<210> SEQ ID NO 18
<211> LENGTH: 150
<212> TYPE: PRT
<213> ORGANISM: Malus domestica
<220> FEATURE:
<223> OTHER INFORMATION: chloroplast vesiculation (CV) MD00G406410
      (Malus domestica-2)

<400> SEQUENCE: 18

Met Thr Val Thr Asn Phe Asn Cys Cys Leu Asn Pro Pro Ser Asn
1               5                   10                  15

Gln Asn His Gly Ser Ser Pro Ser Leu Pro Leu Lys Gln Asn Gln Ala
            20                  25                  30

Leu Ala Trp Asn Lys Tyr Ala His Gly Ser Trp Thr Asn Arg Cys Val
        35                  40                  45

Leu Gly Met Ser Cys Ile Ala Ile Gly Tyr Glu Met Gly Thr Leu Val
    50                  55                  60

Ser Asn Gln Asn Tyr Glu Ala Ile Ala Asn Ala Met Pro Ser Pro Leu
65                  70                  75                  80

Glu Ile Glu Thr Ser Ser Asp Gln Arg Val Ala Lys Trp Ser Asp Lys
                85                  90                  95

Arg Met Cys Pro Gln Trp Ser Pro Asn Ser Leu Glu Thr Ile Val Pro

|       |       |       | 100   |       |       |       | 105   |       |       |       | 110   |       |
|-------|-------|-------|-------|-------|-------|-------|-------|-------|-------|-------|-------|-------|

Glu Asn Leu Pro Arg Pro Ser Ala Gln Met Arg Trp Glu Thr Val Gly
        115                 120                 125

Phe Ser Asp Lys Asp Ala Pro Val Val Gln Met Val Val Arg Lys Gly
    130                 135                 140

Gly Ser Cys Phe Ala Met
145                 150

<210> SEQ ID NO 19
<211> LENGTH: 603
<212> TYPE: DNA
<213> ORGANISM: Malus domestica
<220> FEATURE:
<223> OTHER INFORMATION: chloroplast vesiculation (CV) MD14G005720
      (Malus domestica-3)

<400> SEQUENCE: 19

```
atggcttgtt ttagagggtc accattgagg tctttgtcat ctcttttaac cttatgcaac      60
caaacccacc ttcctctttt gatatatacg atccctctcc ttctgtcatt gcttaaattc     120
agagagaaca gagagagaga gagagagaaa gggatgactg ttacaaactt caattgctgc     180
ctcaatccgc caccttcaaa tcaaaaccat ggttcaagcc cttctttgcc cttaaagaaa     240
aaccaagcac ttgcatggaa caaatatgct catggatcat ggactaatcg atgcgttttr     300
ggtatgagtt gcgcaattgg attggaaatg gaaccctag taagcaacca aaactatgag     360
gccattgcta atgctatgcc ttcgccgttg aaatagaaa catatagtga tcagagggtt     420
gaaaaatgga gtgacaaaag aatatgccca caatggagcc ctaattcaca agagaccatt     480
gtgcctgaaa atctcccaag atcatctgct caaaggagat gggaaacagt tggtttttct     540
aacgaggatg ctccggcggt tcaaatggta gttagaaaag gtggcaactg ctttgctatg     600
tag                                                                  603
```

<210> SEQ ID NO 20
<211> LENGTH: 149
<212> TYPE: PRT
<213> ORGANISM: Malus domestica
<220> FEATURE:
<223> OTHER INFORMATION: chloroplast vesiculation (CV) MD14G005720
      (Malus domestica-3)
<220> FEATURE:
<221> NAME/KEY: VARIANT
<222> LOCATION: (104)...(104)
<223> OTHER INFORMATION: Xaa = any amino acid

<400> SEQUENCE: 20

Met Thr Val Thr Asn Phe Asn Cys Cys Leu Asn Pro Pro Ser Asn
1               5                   10                  15

Gln Ser His Gly Ser Ser Pro Ser Leu Pro Ser Lys Gln Asn Gln Val
            20                  25                  30

Pro Ala Trp Asn Lys Asn Asp His Gly Ser Trp Ala Lys Arg Cys Val
        35                  40                  45

Val Gly Met Ser Cys Ile Met Ile Gly Phe Glu Met Gly Ser Val Val
    50                  55                  60

Ser Asn Gln Thr His Glu Ala Ile Ala Lys Val Met Pro Leu Pro Leu
65                  70                  75                  80

Glu Ile Ala Thr Ser Ser Asp Gln Arg Val Ala Lys Trp Ser Glu Lys
                85                  90                  95

Arg Met Cys Pro Gln Trp Ser Xaa Asn Ser Leu Glu Thr Ile Val Pro
            100                 105                 110

```
Glu Asn Leu Pro Arg Pro Ser Ala Gln Arg Arg Trp Glu Ala Val Gly
        115                 120                 125

Phe Ser Lys Asp Ala Pro Ala Val Gln Met Val Val Arg Lys Gly Gly
    130                 135                 140

Asn Cys Phe Ala Met
145

<210> SEQ ID NO 21
<211> LENGTH: 387
<212> TYPE: DNA
<213> ORGANISM: Manihot esculenta
<220> FEATURE:
<223> OTHER INFORMATION: chloroplast vesiculation (CV) ME00847G01190
      (Manihot esculenta-1)

<400> SEQUENCE: 21
aaattcaaag aaagggtcaa ggcgaatgcg attgccttgg ccgggttgaa gaacgacaag    60
tggagaagcc aatgtttact gggcatggca tgcatcataa ttgggcttga gatggatttg   120
gccagccatg aaaatcttgc ggcggccgaa gatttgcaat tttcacttgg ggaatctaag   180
gagaaaacca agagatacag atggagtgac aaaagaatgt gtcctccatg gcgtcttaat   240
gcactagaga ccattgtgcc tgagaaccta ccaaggccat cagctcgacg gagatgggag   300
gcgattgatt attcaaagat tgttccagct ccggctccgg caattaaagt gataatcaga   360
agcagcaaga attgctttac tatgtaa                                       387

<210> SEQ ID NO 22
<211> LENGTH: 128
<212> TYPE: PRT
<213> ORGANISM: Manihot esculenta
<220> FEATURE:
<223> OTHER INFORMATION: chloroplast vesiculation (CV) ME00847G01190
      (Manihot esculenta-1)

<400> SEQUENCE: 22

Lys Phe Lys Glu Arg Val Lys Ala Asn Ala Ile Ala Leu Ala Gly Leu
1               5                   10                  15

Lys Asn Asp Lys Trp Arg Ser Gln Cys Leu Leu Gly Met Ala Cys Ile
            20                  25                  30

Ile Ile Gly Leu Glu Met Asp Leu Ala Ser His Glu Asn Leu Ala Ala
        35                  40                  45

Ala Glu Asp Leu Gln Phe Ser Leu Gly Glu Ser Lys Glu Lys Thr Lys
    50                  55                  60

Arg Tyr Arg Trp Ser Asp Lys Arg Met Cys Pro Pro Trp Arg Leu Asn
65                  70                  75                  80

Ala Leu Glu Thr Ile Val Pro Glu Asn Leu Pro Arg Pro Ser Ala Arg
                85                  90                  95

Arg Arg Trp Glu Ala Ile Asp Tyr Ser Lys Ile Val Pro Ala Pro Ala
            100                 105                 110

Pro Ala Ile Lys Val Ile Ile Arg Ser Ser Lys Asn Cys Phe Thr Met
        115                 120                 125

<210> SEQ ID NO 23
<211> LENGTH: 435
<212> TYPE: DNA
<213> ORGANISM: Manihot esculenta
<220> FEATURE:
<223> OTHER INFORMATION: chloroplast vesiculation (CV) ME04796G00360
      (Manihot esculenta-2)
```

<400> SEQUENCE: 23

```
atggccattg cacccagttg ctgcctcaat ctccgccctc caactccacc ctcacctcct      60
cccaatgcaa gggctaccca agctgcatgg ttcaagaacg gcagctggag aagccagtgt     120
gtagtgggca tggcctgcat cataattgga gttgaaatgg atttggcgag tcaagcaaat     180
gttgccacag ccaaagactt gcaatattta cttgtagagt cgaaggagaa caccaaaggt     240
gacagatgga gtgacagaag aatttgtcct ccttggcatc ttaattcgct agagaccatt     300
gtgccggaga accttccaag gccgtcggct cgtcggagat gggaagaggt tggtaatgta     360
aagaatgttc cggctccggc gattaaagtg atagttaaaa gccgtagcag cagcaacaat     420
tgctttacca tgtaa                                                     435
```

<210> SEQ ID NO 24
<211> LENGTH: 144
<212> TYPE: PRT
<213> ORGANISM: Manihot esculenta
<220> FEATURE:
<223> OTHER INFORMATION: chloroplast vesiculation (CV) ME04796G00360
      (Manihot esculenta-2)

<400> SEQUENCE: 24

```
Met Ala Ile Ala Pro Ser Cys Cys Leu Asn Leu Arg Pro Pro Thr Pro
1               5                   10                  15
Pro Ser Pro Pro Asn Ala Arg Ala Thr Gln Ala Ala Trp Phe Lys
            20                  25                  30
Asn Gly Ser Trp Arg Ser Gln Cys Val Val Gly Met Ala Cys Ile Ile
        35                  40                  45
Ile Gly Val Glu Met Asp Leu Ala Ser Gln Ala Asn Val Ala Thr Ala
    50                  55                  60
Lys Asp Leu Gln Tyr Leu Leu Val Glu Ser Lys Glu Asn Thr Lys Gly
65                  70                  75                  80
Asp Arg Trp Ser Asp Arg Arg Ile Cys Pro Pro Trp His Leu Asn Ser
                85                  90                  95
Leu Glu Thr Ile Val Pro Glu Asn Leu Pro Arg Pro Ser Ala Arg Arg
            100                 105                 110
Arg Trp Glu Glu Val Gly Asn Val Lys Asn Val Pro Ala Pro Ala Ile
        115                 120                 125
Lys Val Ile Val Lys Ser Arg Ser Ser Asn Asn Cys Phe Thr Met
    130                 135                 140
```

<210> SEQ ID NO 25
<211> LENGTH: 480
<212> TYPE: DNA
<213> ORGANISM: Medicago truncatula
<220> FEATURE:
<223> OTHER INFORMATION: chloroplast vesiculation (CV) MT3G107890

<400> SEQUENCE: 25

```
atgacatcaa ccagttgctg cctccgtctt taccctacaa cttcaaacgc ttctctcatc      60
cctaaaaact cacctcaact ttcctcggag atcaaaaaca gtggatgctg agaaggcgg     120
tgtgttgtga taggagtggc ttcgtgcttc tctataattg gactacaatt caacaattca     180
gtgtcattgg aacatgaagc tgtggctaag agaataccac tgttggtggc catgtcaaat     240
tcaatagatg atgatgatga gcatgtgttt ttggttggtg gtgcggccaa atggagccag     300
aaaaggatgt gcccctcttg gcaaggaaac aatcccctcg aaaccatcgt gccagagaat     360
cttccacggc cagcagcacg tcggagatat gagactgttc gctccacctc taagattgct     420
```
ccaccactct caatgtccgt caaacttaaa accaataggg acagttgttt ctccatgtga    480

<210> SEQ ID NO 26
<211> LENGTH: 159
<212> TYPE: PRT
<213> ORGANISM: Medicago truncatula
<220> FEATURE:
<223> OTHER INFORMATION: chloroplast vesiculation (CV) MT3G107890

<400> SEQUENCE: 26

Met Thr Ser Thr Ser Cys Cys Leu Arg Leu Tyr Pro Thr Thr Ser Asn
1               5                   10                  15

Ala Ser Leu Ile Pro Lys Asn Ser Pro Gln Leu Ser Ser Glu Ile Lys
            20                  25                  30

Asn Ser Gly Cys Trp Arg Arg Arg Cys Val Val Ile Gly Val Ala Ser
        35                  40                  45

Cys Phe Ser Ile Ile Gly Leu Gln Phe Asn Asn Ser Val Ser Leu Glu
    50                  55                  60

His Glu Ala Val Ala Lys Glu Asn Thr Met Leu Val Ala Met Ser Asn
65                  70                  75                  80

Ser Ile Asp Asp Asp Glu His Val Phe Leu Val Gly Gly Ala Ala
                85                  90                  95

Lys Trp Ser Gln Lys Arg Met Cys Pro Ser Trp Gln Gly Asn Asn Pro
            100                 105                 110

Leu Glu Thr Ile Val Pro Glu Asn Leu Pro Arg Pro Ala Ala Arg Arg
        115                 120                 125

Arg Tyr Glu Thr Val Arg Ser Thr Ser Lys Ile Ala Pro Pro Leu Ser
    130                 135                 140

Met Ser Val Lys Leu Lys Thr Asn Arg Asp Ser Cys Phe Ser Met
145                 150                 155

<210> SEQ ID NO 27
<211> LENGTH: 432
<212> TYPE: DNA
<213> ORGANISM: Vitis vinifera
<220> FEATURE:
<223> OTHER INFORMATION: chloroplast vesiculation (CV) FQ394381

<400> SEQUENCE: 27
atggccttct ctgctggttg ctgcctcaat ctctcgcctc caccatctgg gtccagccca    60
cgatcttctc gaagctcaac taaaactgat caagtttcat ggccaagaaa agaaaattca    120
ttgaagagca atgtctcgt ggggttgaca tgcatgataa taagcttaga aatgtccaat    180
ttaatgagtg gtgaagggct ggccattgcc caagatttgc aattaattgg tgaaagaaaa    240
gaggtaacga ggtggagcga caagagaatg tgcccgccct ggcagctcaa ctcattggag    300
acaattgtgc cggagaacct tccccggccg tcgactcgcc ggagatggga gtcagttggt    360
cattccacaa ctgccccggc agtaaaaatt ctatttagag ctcacaccaa gtcagattgt    420
ttttccatgt ga                                                       432

<210> SEQ ID NO 28
<211> LENGTH: 143
<212> TYPE: PRT
<213> ORGANISM: Vitis vinifera
<220> FEATURE:
<223> OTHER INFORMATION: chloroplast vesiculation (CV) FQ394381

<400> SEQUENCE: 28

```
Met Ala Phe Ser Ala Gly Cys Cys Leu Asn Leu Ser Pro Pro Ser
1               5                   10                  15

Gly Ser Ser Pro Arg Ser Ser Arg Ser Ser Thr Lys Thr Asp Gln Val
                20                  25                  30

Ser Trp Pro Arg Lys Glu Asn Ser Leu Lys Ser Lys Cys Leu Val Gly
            35                  40                  45

Leu Thr Cys Met Ile Ile Ser Leu Glu Met Ser Asn Leu Met Ser Gly
    50                  55                  60

Glu Gly Leu Ala Ile Ala Gln Asp Leu Gln Leu Ile Gly Glu Arg Lys
65                  70                  75                  80

Glu Val Thr Arg Trp Ser Asp Lys Arg Met Cys Pro Pro Trp Gln Leu
                85                  90                  95

Asn Ser Leu Glu Thr Ile Val Pro Glu Asn Leu Pro Arg Pro Ser Thr
            100                 105                 110

Arg Arg Arg Trp Glu Ser Val Gly His Ser Thr Thr Ala Pro Ala Val
        115                 120                 125

Lys Ile Leu Phe Arg Ala His Thr Lys Ser Asp Cys Phe Ser Met
    130                 135                 140

<210> SEQ ID NO 29
<211> LENGTH: 423
<212> TYPE: DNA
<213> ORGANISM: Oryza sativa
<220> FEATURE:
<223> OTHER INFORMATION: chloroplast vesiculation (CV) Os05g49940

<400> SEQUENCE: 29
atggtggtct cctgccagct caagcctgcg ccggctccgg ccgccgccag cagaggcggc      60
ggcgcgcctc acctccagca gctgcgccgg gcgtgcgtcg cggcggcggc ggcgtgcgcg     120
gtgctcggga cggcgggcgg ccccggcgaa ggcgccgtga tggcgcgtgc gccggaggcg     180
acggcggcgg cggcggcggg gccggcgcgg tggagcgacc gccggcagtg cccgccgtgg     240
cgcgccaact cgctggagaa catcgtgccg gagaacctgc cgcggccgtc ggctcgccgg     300
aggttcaaca gcatcaccgg ggcggcggcg gcggagagcg cgccgccccc cgcgtcggcg     360
tcgcccgacg ccgtgctccc gttcttggcg ccgcgctccg gcatgggctg cttctcccct     420
taa                                                                  423

<210> SEQ ID NO 30
<211> LENGTH: 140
<212> TYPE: PRT
<213> ORGANISM: Oryza sativa
<220> FEATURE:
<223> OTHER INFORMATION: chloroplast vesiculation (CV) Os05g49940

<400> SEQUENCE: 30

Met Val Val Ser Cys Gln Leu Lys Pro Ala Pro Ala Pro Ala Ala
1               5                   10                  15

Ser Arg Gly Gly Gly Ala Pro His Leu Gln Gln Leu Arg Arg Ala Cys
                20                  25                  30

Val Ala Ala Ala Ala Cys Ala Val Leu Gly Thr Ala Gly Gly Pro
            35                  40                  45

Gly Glu Gly Ala Val Met Ala Arg Ala Pro Glu Ala Thr Ala Ala Ala
    50                  55                  60

Ala Ala Gly Pro Ala Arg Trp Ser Asp Arg Arg Gln Cys Pro Pro Trp
65                  70                  75                  80

Arg Ala Asn Ser Leu Glu Asn Ile Val Pro Glu Asn Leu Pro Arg Pro
```

```
                    85                  90                  95

Ser Ala Arg Arg Arg Phe Asn Ser Ile Thr Ala Ala Ala Ala Glu
            100                 105                 110

Ser Ala Pro Pro Ala Ser Ala Ser Pro Asp Ala Val Leu Pro Phe
        115                 120                 125

Leu Ala Pro Arg Ser Gly Met Gly Cys Phe Ser Leu
    130                 135                 140

<210> SEQ ID NO 31
<211> LENGTH: 435
<212> TYPE: DNA
<213> ORGANISM: Populus trichocarpa
<220> FEATURE:
<223> OTHER INFORMATION: chloroplast vesiculation (CV) PT06G24730

<400> SEQUENCE: 31
atggccatca gaactacttg tcgcctcaat ctctcccctc aggctctgg ctcaaccctc        60 ccttcttcct ctacaaagaa ctcccaggtt gcctggttca agaatgaaaa gtggaggaat     120
cgatgtgtac tgggcgcggc gtgcatgata attggacttg aaatgggagg tggtttagtg     180
ggtggtgaag atcttgccat ggctagggag atgcaggtgg ctgtggaatc aaaagaaaac     240
ttgaatgggc aaggtggag tgacaagaga atgtgccctc catggagtcg aattcgcta      300 gagactattg tgccggagaa ccttccaagg ccatcggctc ataggaggtg gaagaagtt     360 cgctttttcca agaacaatgc tccggccgtc aaagtgattg tgatcaaaag aagcaacggt   420
tgcttctcca tgtaa                                                      435

<210> SEQ ID NO 32
<211> LENGTH: 144
<212> TYPE: PRT
<213> ORGANISM: Populus trichocarpa
<220> FEATURE:
<223> OTHER INFORMATION: chloroplast vesiculation (CV) PT06G24730

<400> SEQUENCE: 32

Met Ala Ile Arg Thr Thr Cys Arg Leu Asn Leu Ser Pro Pro Gly Ser
1               5                   10                  15

Gly Ser Thr Leu Pro Ser Ser Ser Thr Lys Asn Ser Gln Val Ala Trp
            20                  25                  30

Phe Lys Asn Glu Lys Trp Arg Asn Arg Cys Val Leu Gly Ala Ala Cys
        35                  40                  45

Met Ile Ile Gly Leu Glu Met Gly Gly Gly Leu Val Gly Gly Glu Asp
    50                  55                  60

Leu Ala Met Ala Arg Glu Met Gln Val Ala Val Glu Ser Lys Glu Asn
65                  70                  75                  80

Leu Asn Gly Pro Arg Trp Ser Asp Lys Arg Met Cys Pro Pro Trp Ser
                85                  90                  95

Arg Asn Ser Leu Glu Thr Ile Val Pro Glu Asn Leu Pro Arg Pro Ser
            100                 105                 110

Ala His Arg Arg Trp Glu Glu Val Arg Phe Ser Lys Asn Asn Ala Pro
        115                 120                 125

Ala Val Lys Val Ile Val Ile Lys Arg Ser Asn Gly Cys Phe Ser Met
    130                 135                 140

<210> SEQ ID NO 33
<211> LENGTH: 468
<212> TYPE: DNA
<213> ORGANISM: Ricinus communis
```

<220> FEATURE:
<223> OTHER INFORMATION: chloroplast vesiculation (CV) RC29912G02840

<400> SEQUENCE: 33

```
atggccatta caactagttg ctgcctcaat atgaatatcc ctcctccaac tagtgcttca      60
agtctacctt cttcttcttc tactacaaag cccactgctc aagcctcttg gttcaagaat     120
gagaagtgga gaagccaatg tgtactaggc atggcctgca tgataattgg acttgaaatg     180
gataacttgg tgaatgaaga aactaatctt gctatggccg cagagaattc ctcatcggtt     240
gtagaattaa aggtgaaacc aaagactaga agatggagtg ataagagaat gtgtcctcca     300
tggaggctaa attcactaga aaccattgtg cctgagaatc ttccaaggcc atcagctcgt     360
cggagatggg aggctactgg ttattctaag attgatccgg ctccggctcc ggcaaggaaa     420
gtgtcagtca aaagcattat gattatggat aattgcttta ccatgtaa                 468
```

<210> SEQ ID NO 34
<211> LENGTH: 155
<212> TYPE: PRT
<213> ORGANISM: Ricinus communis
<220> FEATURE:
<223> OTHER INFORMATION: chloroplast vesiculation (CV) RC29912G02840

<400> SEQUENCE: 34

```
Met Ala Ile Thr Thr Ser Cys Cys Leu Asn Met Asn Ile Pro Pro Pro
  1               5                  10                  15

Thr Ser Ala Ser Ser Leu Pro Ser Ser Ser Ser Thr Thr Lys Pro Thr
             20                  25                  30

Ala Gln Ala Ser Trp Phe Lys Asn Glu Lys Trp Arg Ser Gln Cys Val
         35                  40                  45

Leu Gly Met Ala Cys Met Ile Ile Gly Leu Glu Met Asp Asn Leu Val
     50                  55                  60

Asn Glu Glu Thr Asn Leu Ala Met Ala Ala Glu Asn Ser Ser Ser Val
 65                  70                  75                  80

Val Glu Leu Lys Val Lys Pro Lys Thr Arg Arg Trp Ser Asp Lys Arg
                 85                  90                  95

Met Cys Pro Pro Trp Arg Leu Asn Ser Leu Glu Thr Ile Val Pro Glu
            100                 105                 110

Asn Leu Pro Arg Pro Ser Ala Arg Arg Arg Trp Glu Ala Thr Gly Tyr
        115                 120                 125

Ser Lys Ile Asp Pro Ala Pro Ala Pro Ala Arg Lys Val Ser Val Lys
    130                 135                 140

Ser Ile Met Ile Met Asp Asn Cys Phe Thr Met
145                 150                 155
```

<210> SEQ ID NO 35
<211> LENGTH: 726
<212> TYPE: DNA
<213> ORGANISM: Solanum lycopersicum
<220> FEATURE:
<223> OTHER INFORMATION: chloroplast vesiculation (CV) Solyc08g067630

<400> SEQUENCE: 35

```
atggctattt caacaaagtt ctgcctcaat ctctcccctc aacctcctcc tacttctaat      60
tataataact caattccccc accttcaaaa aaaactcaac tttcttggta agtctactac     120
tacttttttac attttttttt atttatcata ctttgctttt cgttttttgga tgtttgtcta     180
tgttaaaagt cgtgtgcatc atgtccatat ctattcatcc atttcaattt atgtgatatt     240
```

-continued

```
atatatgttc attcatctgt ttcattttat acgacattat atatatatat atatatatat     300
atatacattc aattgtttca ctttatatga ttaaatttttt tattaattta aactactatt     360
ttcatttttt ttcgcaggca acgaaaagaa aaatcatgga aaaatcaatg tgtattagga     420
atggcatgtg ttgtaattat tggattagaa tttgacgatt caattttagt taatcaagaa     480
agtacgatcg cgatcgccgg agacatgcaa ttacaatatg tcgccggaaa atcaatacaa     540
aaatggagtg aaaaaagatc atgcccaccg tggaacgtga actcgttaga aaccatcgtg     600
ccggaaaact taccgaggcc ggtgactcgc cggagatggg aaaacgttga ttataatact     660
actactcaat ctgcacctga agtaaagttg gtgacaaaat ttagtaaagg atgtttcact     720
atgtga                                                                726
```

<210> SEQ ID NO 36
<211> LENGTH: 151
<212> TYPE: PRT
<213> ORGANISM: Solanum lycopersicum
<220> FEATURE:
<223> OTHER INFORMATION: chloroplast vesiculation (CV) Solyc08g067630

<400> SEQUENCE: 36

```
Met Ala Ile Ser Thr Lys Phe Cys Leu Asn Leu Ser Pro Gln Pro Pro
1               5                   10                  15

Pro Thr Ser Asn Tyr Asn Asn Ser Ile Pro Pro Ser Lys Lys Thr
            20                  25                  30

Gln Leu Ser Trp Gln Arg Lys Glu Lys Ser Trp Lys Asn Gln Cys Val
        35                  40                  45

Leu Gly Met Ala Cys Val Val Ile Ile Gly Leu Glu Phe Asp Asp Ser
    50                  55                  60

Ile Leu Val Asn Gln Glu Ser Thr Ile Ala Ile Ala Gly Asp Met Gln
65                  70                  75                  80

Leu Gln Tyr Val Ala Gly Lys Ser Ile Gln Lys Trp Ser Glu Lys Arg
                85                  90                  95

Ser Cys Pro Pro Trp Asn Val Asn Ser Leu Glu Thr Ile Val Pro Glu
            100                 105                 110

Asn Leu Pro Arg Pro Val Thr Arg Arg Arg Trp Glu Asn Val Asp Tyr
        115                 120                 125

Asn Thr Thr Thr Gln Ser Ala Pro Glu Val Lys Leu Val Thr Lys Phe
    130                 135                 140

Ser Lys Gly Cys Phe Thr Met
145                 150
```

<210> SEQ ID NO 37
<211> LENGTH: 474
<212> TYPE: DNA
<213> ORGANISM: Sorghum bicolor
<220> FEATURE:
<223> OTHER INFORMATION: chloroplast vesiculation (CV) SB09G029300
      (Sorghum bicolor-1)

<400> SEQUENCE: 37

```
atggcggtct cctccatcag ctgctcccct cggcctccag ctcccgtcag agaagcttcc     60
gctcgtctga cgccgccgca gccgtcgcca ccaaagacga cggccacgcc gtgggcggac    120
gggctgcggc gggcatgcgt ggcggcggcg gcaaccgcgg cgtgcgtcgt gatcgggacg    180
gcgggaggtg cgacgtggt ggcggcgtcg atgccacgcg acacccccgt tctggctgtg    240
gacgcgcggc cggcggcggc ggcgccgcgg tggagcgacc gcagggagtg cccgccgtgg    300
```

-continued

```
cgcgctaact cgctggagaa catcgtgccg gagaacctgc cccgcccgtc ggcgcgccgg    360
aggttcaaca cagtcaagcg agcgccgcgg aaggccccg cgctcgggcg tcaagcggtg    420
gcgccgccgt tcctggcgct gcgctccggc gtggacgact gcttcaccct ctag        474
```

<210> SEQ ID NO 38
<211> LENGTH: 157
<212> TYPE: PRT
<213> ORGANISM: Sorghum bicolor
<220> FEATURE:
<223> OTHER INFORMATION: chloroplast vesiculation (CV) SB09G029300
      (Sorghum bicolor-1)

<400> SEQUENCE: 38

```
Met Ala Val Ser Ser Ile Ser Cys Ser Leu Arg Pro Ala Pro Val
1               5                  10                  15

Arg Glu Ala Ser Ala Arg Leu Thr Pro Pro Gln Pro Ser Pro Lys
                20                  25                  30

Thr Thr Ala Thr Pro Trp Ala Asp Gly Leu Arg Arg Ala Cys Val Ala
            35                  40                  45

Ala Ala Ala Thr Ala Ala Cys Val Val Ile Gly Thr Ala Gly Gly Gly
        50                  55                  60

Asp Val Val Ala Ala Ser Met Pro Arg Asp Thr Pro Val Leu Ala Val
65                  70                  75                  80

Asp Ala Arg Pro Ala Ala Ala Pro Arg Trp Ser Asp Arg Glu
                85                  90                  95

Cys Pro Pro Trp Arg Ala Asn Ser Leu Glu Asn Ile Val Pro Glu Asn
                100                 105                 110

Leu Pro Arg Pro Ser Ala Arg Arg Phe Asn Thr Val Lys Arg Ala
            115                 120                 125

Pro Arg Lys Ala Pro Ala Leu Gly Arg Gln Ala Val Ala Pro Pro Phe
        130                 135                 140

Leu Ala Leu Arg Ser Gly Val Asp Asp Cys Phe Thr Leu
145                 150                 155
```

<210> SEQ ID NO 39
<211> LENGTH: 498
<212> TYPE: DNA
<213> ORGANISM: Sorghum bicolor
<220> FEATURE:
<223> OTHER INFORMATION: chloroplast vesiculation (CV) SB09G029310
      (Sorghum bicolor-2)

<400> SEQUENCE: 39

```
atggcggctt cctccaccgc caccaccata atcagctgct gctgctgctg cctcgggcct    60
cccgctccgc ccaaagaatc ctctgcaggc gctcgcaggc gcaggcgcc ggcaggcgtg    120 tcagtgtcgt cgcacgcgct gcgccgggcg tgcgtggctg ccgcggcgtg cgcgatggtg    180
gggatttcgg gcggcggcgg cggcgccgac atggcccttg cgctggcgcg tggcggcggc    240
gcgttcgcct ccaggaccga cgtcgtcgcc gtgtccgtgg gcgccgcgcg cgccaaggcg    300
ccgccgcggt ggagcgaccg caggcagtgc ccgccgtggc gcgccaactc gctggagaac    360
atcgtgccgg agaacctgcc ccgcccgtcc gcgcccagga ggttcgacag cgtctcggcc    420
tcggcggccg cgccggactt gtcggcgccg ccttcttcc tggcgctgcg acccggcacg    480
ggctgcttct cactctga                                                  498
```

<210> SEQ ID NO 40
<211> LENGTH: 165

```
<212> TYPE: PRT
<213> ORGANISM: Sorghum bicolor
<220> FEATURE:
<223> OTHER INFORMATION: chloroplast vesiculation (CV) SB09G029310
      (Sorghum bicolor-2)

<400> SEQUENCE: 40

Met Ala Ala Ser Ser Thr Ala Thr Thr Ile Ile Ser Cys Cys Cys Cys
1               5                   10                  15

Cys Leu Gly Pro Pro Ala Pro Pro Lys Glu Ser Ser Ala Gly Ala Arg
            20                  25                  30

Arg Pro Gln Ala Pro Ala Gly Val Ser Val Ser Ser His Ala Leu Arg
        35                  40                  45

Arg Ala Cys Val Ala Ala Ala Cys Ala Met Val Gly Ile Ser Gly
    50                  55                  60

Gly Gly Gly Gly Ala Asp Met Ala Leu Ala Leu Ala Arg Gly Gly Gly
65                  70                  75                  80

Ala Phe Ala Ser Arg Thr Asp Val Val Ala Val Ser Val Gly Ala Ala
                85                  90                  95

Arg Ala Lys Ala Pro Pro Arg Trp Ser Asp Arg Gln Cys Pro Pro
            100                 105                 110

Trp Arg Ala Asn Ser Leu Glu Asn Ile Val Pro Glu Asn Leu Pro Arg
            115                 120                 125

Pro Ser Ala Pro Arg Arg Phe Asp Ser Val Ser Ala Ser Ala Ala Ala
        130                 135                 140

Pro Asp Leu Ser Ala Pro Pro Ser Phe Leu Ala Leu Arg Pro Gly Thr
145                 150                 155                 160

Gly Cys Phe Ser Leu
                165

<210> SEQ ID NO 41
<211> LENGTH: 426
<212> TYPE: DNA
<213> ORGANISM: Theobroma cacao
<220> FEATURE:
<223> OTHER INFORMATION: chloroplast vesiculation (CV) TC09G013320

<400> SEQUENCE: 41
atggccattt caactaggtg ctgcctcaat gtgtcccctc caactccaac tcctggcttt      60
gacatgtctt cttctaacaa gaaggcatcc caagttgcat ggccaaggga tgataaatgg     120
aggaagcaat gtgtactagg ggtaacctgc atcgtaattg gattacaagt aggtaatata     180
actgacaaca gcgccattgc tgaggaagtc tcatctgcca cagagtcaaa ctcgaaagta     240
gcaagatgga gtgataaaag agtgtgccct ccatggaatg caaattcgct ggagaccatc     300
gtgccggaga atctcccacg accatcagct catagaagat gggaagctat tggtttctcc     360
aagaatgccc cggcagtcag agtgaaagtg acaacaaaaa caagaaccaa ttgcttctcc     420
atgtaa                                                                 426

<210> SEQ ID NO 42
<211> LENGTH: 141
<212> TYPE: PRT
<213> ORGANISM: Theobroma cacao
<220> FEATURE:
<223> OTHER INFORMATION: chloroplast vesiculation (CV) TC09G013320

<400> SEQUENCE: 42

Met Ala Ile Ser Thr Arg Cys Cys Leu Asn Val Ser Pro Pro Thr Pro
1               5                   10                  15
```

```
Thr Pro Gly Phe Asp Met Ser Ser Asn Lys Lys Ala Ser Gln Val
            20                  25                  30

Ala Trp Pro Arg Asp Asp Lys Trp Arg Lys Gln Cys Val Leu Gly Val
        35                  40                  45

Thr Cys Ile Val Ile Gly Leu Gln Val Gly Asn Ile Thr Asp Asn Ser
50                  55                  60

Ala Ile Ala Glu Glu Val Ser Ser Ala Thr Glu Ser Asn Ser Lys Val
65                  70                  75                  80

Ala Arg Trp Ser Asp Lys Arg Val Cys Pro Pro Trp Asn Ala Asn Ser
                85                  90                  95

Leu Glu Thr Ile Val Pro Glu Asn Leu Pro Arg Pro Ser Ala His Arg
            100                 105                 110

Arg Trp Glu Ala Ile Gly Phe Ser Lys Asn Ala Pro Ala Val Arg Val
        115                 120                 125

Lys Val Thr Thr Lys Thr Arg Thr Asn Cys Phe Ser Met
130                 135                 140

<210> SEQ ID NO 43
<211> LENGTH: 360
<212> TYPE: DNA
<213> ORGANISM: Zea mays
<220> FEATURE:
<223> OTHER INFORMATION: chloroplast vesiculation (CV) AZ916442

<400> SEQUENCE: 43
ccgtttcacc gttatatctg cagggcggac gggctgcggc gggcgtgcgt ggcgggcgcg      60
gcggcgtgcg tcgtgttcgg gacggcggga ggcggcggcg gcggcgtggc cgcgtcggcg     120
ccgccgcgcg acgcctccgt cgcggcggcc ccgcggtgga cgaccgccgg ggagtgcccg     180
ccgtggcgcg ccaactcgct ggagaacgtc gtgccggaga acctgccccg ccgtcggcg      240 cgccggaggt tcagcaccgt caagcgggcg ccgcggaagg cccccgcgct cgggcctcag     300
gcggtggcgc cgtcgccgtt cctggcgctg cgatccggca tggacgactg cttcaccctc     360

<210> SEQ ID NO 44
<211> LENGTH: 120
<212> TYPE: PRT
<213> ORGANISM: Zea mays
<220> FEATURE:
<223> OTHER INFORMATION: chloroplast vesiculation (CV) AZ916442

<400> SEQUENCE: 44

Pro Phe His Arg Tyr Ile Cys Arg Ala Asp Gly Leu Arg Arg Ala Cys
1               5                   10                  15

Val Ala Gly Ala Ala Cys Val Val Phe Gly Thr Ala Gly Gly Gly
            20                  25                  30

Gly Gly Gly Val Ala Ala Ser Ala Pro Pro Arg Asp Ala Ser Val Ala
        35                  40                  45

Ala Ala Pro Arg Trp Ser Asp Arg Glu Cys Pro Pro Trp Arg Ala
    50                  55                  60

Asn Ser Leu Glu Asn Val Val Pro Glu Asn Leu Pro Arg Pro Ser Ala
65                  70                  75                  80

Arg Arg Arg Phe Ser Thr Val Lys Arg Ala Pro Arg Lys Ala Pro Ala
                85                  90                  95

Leu Gly Pro Gln Ala Val Ala Pro Ser Pro Phe Leu Ala Leu Arg Ser
            100                 105                 110

Gly Met Asp Asp Cys Phe Thr Leu
        115                 120
```

```
<210> SEQ ID NO 45
<211> LENGTH: 9
<212> TYPE: PRT
<213> ORGANISM: Artificial Sequence
<220> FEATURE:
<223> OTHER INFORMATION: synthetic chloroplast vesiculation (CV)
      consensus sequence
<220> FEATURE:
<221> NAME/KEY: VARIANT
<222> LOCATION: (2)...(8)
<223> OTHER INFORMATION: Xaa = any amino acid

<400> SEQUENCE: 45

Arg Xaa Cys Xaa Xaa Trp Xaa Xaa Asn
1               5

<210> SEQ ID NO 46
<211> LENGTH: 16
<212> TYPE: PRT
<213> ORGANISM: Artificial Sequence
<220> FEATURE:
<223> OTHER INFORMATION: synthetic chloroplast vesiculation (CV)
      consensus sequence
<220> FEATURE:
<221> NAME/KEY: VARIANT
<222> LOCATION: (2)...(15)
<223> OTHER INFORMATION: Xaa = any amino acid

<400> SEQUENCE: 46

Glu Xaa Xaa Xaa Pro Glu Asn Leu Pro Arg Xaa Xaa Xaa Xaa Xaa Arg
1               5                   10                  15

<210> SEQ ID NO 47
<211> LENGTH: 21
<212> TYPE: DNA
<213> ORGANISM: Artificial Sequence
<220> FEATURE:
<223> OTHER INFORMATION: synthetic miRNA targeting chloroplast
      vesiculation (CV) At2G25625 (AtCV) (amiR-AtCV)

<400> SEQUENCE: 47
ttacacgtaa tgaacttcca g                                              21

<210> SEQ ID NO 48
<211> LENGTH: 8
<212> TYPE: PRT
<213> ORGANISM: Artificial Sequence
<220> FEATURE:
<223> OTHER INFORMATION: synthetic linker between chloroplast
      vesiculation (CV) At2G25625 (AtCV) and green fluorescence protein
      (GFP)

<400> SEQUENCE: 48

Gly Gly Ala Ala Gly Gly Ala Ala
1               5
```

PLANT TOLERANCE TO STRESS THROUGH THE CONTROL OF CHLOROPLAST STABILITY

CROSS-REFERENCE TO RELATED APPLICATIONS

This application is a continuation of U.S. application Ser. No. 15/030,355, filed Apr. 18, 2016, which is a US National Stage of International Application No. PCT/US2014/062900, filed Oct. 29, 2014, which claims benefit under 35 U.S.C. § 119(e) of U.S. Provisional Application No. 61/897,006, filed Oct. 29, 2013, the contents of each of which are incorporated herein by reference for all purposes.

REFERENCE TO SEQUENCE LISTING

This application includes a Sequence Listing as a text file named "Seq-text-file-1139168.txt" created May 7, 2019, and containing 46,874 bytes. The material contained in this text file is incorporated by reference in its entirety for all purposes.

FIELD OF THE INVENTION

This invention relates to plants having increased tolerance to stress or having enhanced nutrient assimilation in sink tissues, and methods of preparing the plants.

BACKGROUND OF THE INVENTION

Environmental stress such as high salinity, extreme temperatures, and drought are responsible for high yield loses of major crops worldwide (Mittler and Blumwald 2010, Annual Review Of Plant Biology 61: 443-462). Plants use an escape strategy to cope with stress, which is characterized by early flowering and leaf senescence (Levitt 1972, Annu Rev Plant Biol 58: 115-136; Ludlow 1989, Strategies in response to water stress. SPB Academic Press, The Netherlands; Mittler and Blumwald 2010, Annual Review Of Plant Biology 61: 443-462). During leaf senescence, the earliest event is the degradation of the chloroplasts that possess up to 70% of total leaf proteins (Lim et al. 2007; Ishida et al. 2008, Plant Physiol 148: 142-155). The mobile nitrogen resulting from chloroplast disassembly is recycled and supplied to the sink organs, flowers and seeds (Liu et al. 2008 J Plant Biol 51: 11-19). However, the stress-induced chloroplast degradation and premature senescence can affect plant photosynthetic capacity and eventually compromise the crop yield.

Although the inhibition of photosynthetic activity and the degradation of the photosynthetic apparatus are a primary target of abiotic stresses (Rivero et al. 2007, Proceedings of the National Academy of Sciences of the United States of America 104: 19631-19636), the mechanisms of stress-induced chloroplast degradation remain largely unknown. As an indispensable step of chloroplast degradation, the chlorophyll breakdown has been investigated in detail in *Arabidopsis* (Hortensteiner 2009, Trends Plant Sci 14: 155-162). Five chlorophyll catabolic enzymes that catalyze green chlorophyll to colorless nonfluorescent chlorophyll catabolites, which are finally disposed in the vacuole, have been identified (Hortensteiner 2006 Annual Review of Plant Biology 57: 55-77; Hortensteiner 2009 Trends Plant Sci 14: 155-162); Sakuraba et al. 2012, Plant Cell 24: 507-518). Recently, SGR a gene encoding a nonenzyme protein SGR (stay-green) has been shown to be a key factor in chlorophyll degradation (Jiang et al. 2007; Park et al. 2007, Plant Cell 19: 1649-1664; Ren et al. 2007, Plant Physiology 144: 1429-1441). In *Arabidopsis*, the SGR protein (AtNYE1) was able to destabilize the light-harvesting complex II (LHCII) and recruited the five chlorophyll catabolic enzymes to the thylakoids of senescing chloroplast for chlorophyll degradation. After the chlorophyll degradation, the chlorophyll-binding proteins were more susceptible to digestion by chloroplast proteases (Park et al. 2007; Ren et al. 2007, Plant Physiology 144: 1429-1441; Hortensteiner 2009; Sakuraba et al. 2012, Plant Cell 24: 507-518).

Two pathways have been demonstrated for the degradation of chloroplast stromal proteins: autophagy (Ishida and Yoshimoto 2008 Autophagy 4: 961-962; Ishida et al. 2008, Plant Physiol 148: 142-155; Wada et al. 2009, Plant Physiol 149: 885-893; Izumi et al. 2010, Plant Physiol 154: 1196-1209) and senescence-associated vacuoles (SAV) (Otegui et al. 2005, Plant Journal 41: 831-844; Martinez et al. 2008, Plant Journal 56: 196-206; Carrion et al. 2013). Autophagy is a well-known system for the bulk degradation of intracellular proteins and organelles (Ohsumi 2001, Nature Reviews Molecular Cell Biology 2: 211-216; Bassham 2009, Biochim Biophys Acta 1793: 1397-1403). Plant autophagy has been shown to function in senescence, defense against pathogens and response to abiotic stress (Bassham, 2009 Biochim Biophys Acta 1793: 1397-1403; Reumann et al. 2010, Protoplasma 247: 233-256; Liu and Bassham 2012, Annu Rev Plant Biol 63: 215-237). The chloroplast Rubisco protein and stroma-targeted fluorescent proteins were shown to move to the vacuole via autophagic bodies named Rubisco-containing bodies (RCBs). Dark-induced chloroplast degradation and RCBs formation were impaired in autophagy-defective mutants (Ishida and Yoshimoto 2008, Autophagy 4: 961-962; Ishida et al. 2008, Plant Physiol 148: 142-155; Wada et al. 2009, Plant Physiol 149: 885-893). Even whole chloroplasts have been shown to be transported to the vacuole through the autophagy-dependent process in individually darkened leaves (Ishida and Wada 2009 Autophagy 5: 736-737; Wada et al. 2009, Plant Physiol 149: 885-893). Interestingly, RCBs-mediated chloroplast degradation was highly activated by the shortage of carbon source rather than nitrogen source (Izumi et al. 2010, Plant Physiol 154: 1196-1209; Izumi and Ishida 2011, Plant Signal Behav 6: 685-687). This observation might be partially explained by studies showing that autophagy also participates in chloroplast starch degradation by engulfing small starch granule-like structures from chloroplast and transporting them to the vacuole for subsequent breakdown (Wang et al. 2013, Plant Cell 25: 1383-1399).

In spite of the increasing information regarding processes associated with the degradation of chloroplast stroma proteins, the pathway(s) by which thylakoid membrane proteins are released from the chloroplast and transported to the vacuole for degradation remain poorly understood. Thus, the identification and characterization of genes associated with chloroplast destabilization would be useful to develop new plant varieties with altered source/sink interactions and thus provide enhanced nutrient assimilation in desired tissues in the plant. In addition, identification of such genes would also be useful to develop new plant varieties in which chloroplast degradation is inhibited or delayed, thus conferring tolerance to stress conditions on the plants. This invention addresses these and other needs.

BRIEF SUMMARY OF THE INVENTION

The present invention provides methods of preparing a transgenic plant having enhanced stress tolerance. The methods comprise introducing into a population of plants an expression cassette that inhibits expression of a chloroplast vesiculation (CV) gene. In a typical embodiment, the method further includes the step of selecting a plant having enhanced stress tolerance compared to a control plant that does not comprise the expression cassette. The step of introducing the expression cassette can be carried out by any known method such as, for example, using *Agrobacterium*.

In a typical embodiment, the expression cassette comprises a nucleic acid sequence encoding a microRNA or an siRNA specific to the CV gene. The target CV gene may encode a CV protein comprising the consensus sequence RxCxxWxxN (SEQ ID NO: 45) and/or the consensus sequence ExxxPENLPRxxxxxR (SEQ ID NO: 46), where "x" can be any amino acid. Alternatively, the CV gene can encode a polypeptide comprising an amino acid sequence at least 90% identical to any one of SEQ ID NOs: 2, 4, 6, 8, 10, 12, 14, 16, 18, 20, 22, 24, 26, 28, 30, 32, 34, 36, 38, 40, 42, or 44. The target CV gene may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43.

The expression cassette may comprise a constitutive promoter or an inducible promoter. The inducible promoter may be one that is induced in response to stress conditions.

In some embodiments, the transgenic plant has enhanced tolerance to an abiotic stress, such as high salt conditions. In these embodiments, the step of selecting includes selecting plants having enhanced salt tolerance.

In some embodiments, the abiotic stress is drought conditions. In these embodiments, the step of selecting includes selecting plants having enhanced drought tolerance.

The invention also provides plants prepared by the above methods of the invention.

The invention further provides isolated nucleic acid molecules comprising a plant promoter operably linked to a nucleic acid sequence encoding a microRNA or an siRNA specific to a target CV gene. The target CV gene typically encodes a CV protein comprising a consensus sequence as shown in SEQ ID NO: 45 and/or SEQ ID NO: 46 or encodes a polypeptide comprising an amino acid sequence at least 90% identical to any one of SEQ ID NOs: 2, 4, 6, 8, 10, 12, 14, 16, 18, 20, 22, 24, 26, 28, 30, 32, 34, 36, 38, 40, 42, or 44. The target CV gene may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43. The plant promoter may be a constitutive promoter or an inducible promoter.

In other embodiments, the invention provides methods of preparing a transgenic plant having enhanced stress tolerance. These methods comprise (a) introducing mutations in CV genes in a population of plants; and optionally (b) selecting a plant having enhanced stress tolerance compared to a control plant that does not comprise the mutation.

The mutations may be introduced into the plant using chemical mutagenesis. The desired plants can be identified using Targeting Induced Local Lesions in Genomes (TILLING). The invention also provides plants prepared by these methods.

The invention further provides transgenic plants comprising an expression cassette comprising a plant promoter operably linked to a nucleic acid sequence encoding a microRNA or an siRNA specific to a target CV gene. The target CV gene may encode a CV protein comprising a consensus sequence as shown in SEQ ID NO: 45 and/or SEQ ID NO: 46 or encode a polypeptide comprising an amino acid sequence at least 90% identical to any one of SEQ ID NOs: 2, 4, 6, 8, 10, 12, 14, 16, 18, 20, 22, 24, 26, 28, 30, 32, 34, 36, 38, 40, 42, or 44. The target CV gene may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43.

The invention also provides methods of preparing a transgenic plant having enhanced nutrient assimilation. The methods comprise introducing into a population of plants an expression cassette comprising an inducible plant promoter operably linked to a CV polynucleotide sequence encoding a polypeptide at least 90% identical to any one of SEQ ID NOs: 2, 4, 6, 8, 10, 12, 14, 16, 18, 20, 22, 24, 26, 28, 30, 32, 34, 36, 38, 40, 42, or 44. In the typical embodiment, the methods further comprise selecting a plant having enhanced nutrient assimilation compared to a control plant that does not comprise the expression cassette. The CV polynucleotide may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43. The step of introducing the expression cassette may be carried using *Agrobacterium*. The step of selecting may be carried out by selecting plants with increased fruit yield compared to control plants. The invention also provides transgenic plants prepared by these methods.

The invention also provides an expression cassette comprising an inducible plant promoter operably linked to a CV polynucleotide sequence encoding a CV protein comprising a consensus sequence as shown in SEQ ID NO: 45 and/or SEQ ID NO: 46 or encoding a polypeptide comprising an amino acid sequence at least 90% identical to any one of SEQ ID NOs: 2, 4, 6, 8, 10, 12, 14, 16, 18, 20, 22, 24, 26, 28, 30, 32, 34, 36, 38, 40, 42, or 44. The CV polynucleotide may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43. The invention further provides plants comprising the expression cassettes.

Definitions

As used herein, a "stress" (either abiotic or biotic) refers to the exposure of a plant to an agent (living or non-living) or condition that has an adverse effect on metabolism, development, propagation, and/or survival of the plant (collectively "growth").

As used herein, the terms "abiotic stress" or "abiotic stress condition" refer to exposure of a plant to a non-living physical or chemical agent or condition that has an adverse effect on the growth of the plant. Such a stress can be imposed on a plant due, for example, to an environmental factor such as excessive or insufficient water (e.g., flooding, drought, dehydration), anaerobic conditions (e.g., a low level of oxygen), abnormal osmotic conditions, salinity or temperature (e.g., hot/heat, cold, freezing, frost), a deficiency of nutrients or exposure to pollutants, or by a hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue or isolated cell in a liquid medium such as occurs during monsoon, wet season, flash flooding, excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Saline stress (salt-stress) can be associated with or induced by a perturbation in the osmotic potential of the intracellular or extracellular environment of a cell. Osmotic stress also can be associated with or induced by a change, for example, in the concentration of molecules in the intracellular or extracellular environment of a plant cell, particularly where the molecules cannot be partitioned across the plant cell membrane.

As used herein, the term "drought stress" refers to conditions in which evapotranspiration demand for water exceeds the supply of water. Drought tolerant plants of the invention will show better growth and/or recovery from the stress, as compared to drought sensitive (e.g., control) plants. Typically, the drought stress will be at least 5 days and can be as long as 18 to 20 days with little or no added water.

The term "water-use efficiency" refers to the productivity of a plant per unit of water applied. For example, a plant may grow with substantially no yield penalty under extended periods with less than normal (typically about half) amounts of water.

As used herein, the term "salt stress" refers to conditions in which salinity has an adverse effect on growth of a plant. While for each species, the threshold at which soil and/or water salinity differs, a salt-tolerant plant will have a higher salinity threshold before growth or other measures of productivity decline, as compared to a control or reference plant.

As used herein, the term "biotic stress" refers to stress that occurs as a result of damage caused to plants by other living organisms, such as bacteria, viruses, fungi, parasites, insects, birds, mammals or other plants.

A "chloroplast vesiculation (CV) gene" or a "CV polynucleotide" is a gene or nucleic acid sequence (DNA or RNA) comprising at least a portion of a coding region which encodes a CV protein of the invention. A CV polynucleotide may also be an RNA molecule (e.g., short intefering RNA, or micoRNA) transcribed from a CV DNA. The CV polynucleotide may comprise a coding sequence at least 90% identical to any one of SEQ ID NOs: 1, 3, 5, 7, 9, 11, 13, 15, 17, 19, 21, 23, 25, 27, 29, 31, 33, 35, 37, 39, 41, or 43.

A "chloroplast vesiculation (CV) polypeptide" or "CV protein" is a polypeptide or protein which is at least substantially identical to any one of SEQ ID NOs: 2, 4, 6, 8, 10, 12, 14, 16, 18, 20, 22, 24, 26, 28, 30, 32, 34, 36, 38, 40, 42, or 44 and which controls chloroplast stability in plant cells. CV polypeptide or protein can also be identified by the presence of the consensus sequence as shown here. In some embodiments, the CV polypeptide or protein may comprise either or both of the following consensus sequences: RxCxxWxxN (SEQ ID NO: 45) or ExxxPENLPRxxxxxR (SEQ ID NO: 46), where "x" can be any amino acid. A CV polypeptide of the invention typically comprises about 50 to about 195 amino acids, often between about 100 and about 150 amino acids.

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter the expression of a polypeptide encoded by that nucleic acid.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "constitutive" or "constitutively" denotes temporal and spatial expression of the CV polypeptides or nucleic acids of the present invention in plants in the methods according to various exemplary embodiments of the invention. The term "constitutive" or "constitutively" means the expression of the polypeptides or nucleic acids of the present invention in the tissues of the plant throughout the life of the plant and in particular during its entire vegetative cycle. In some embodiments, the polypeptides or nucleic acids are expressed constitutively in all plant tissues. In some embodiments, the polypeptides or nucleic acids are expressed constitutively in the roots, the leaves, the stems, the flowers, and/or the fruits. In other embodiments of the invention, the polypeptides or nucleic acids are expressed constitutively in the roots, the leaves, and/or the stems.

The term "inducible" or "inducibly" means the CV polypeptides or nucleic acids of the present invention are not expressed, or are expressed at very low levels, in the absence of an inducing agent. The expression of the polypeptides of the present invention is greatly induced in response to an inducing agent.

The term "inducing agent" is used to refer to a chemical, biological or physical agent or environmental condition that effects transcription from an inducible regulatory element. In response to exposure to an inducing agent, transcription from the inducible regulatory element generally is initiated de novo or is increased above a basal or constitutive level of expression. Such induction can be identified using the methods disclosed herein, including detecting an increased level of RNA transcribed from a nucleotide sequence operatively linked to the regulatory element, increased expression of a polypeptide encoded by the nucleotide sequence, or a phenotype conferred by expression of the encoded polypeptide.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

The term "expression cassette" refers to any recombinant expression system for the purpose of expressing a CV nucleic acid sequence of the invention in vitro or in vivo, constitutively or inducibly, in any cell, including, in addition to plant cells, prokaryotic, yeast, fungal, insect or mammalian cells. The expression cassettes of the invention typically comprise a plant promoter operably linked to a CV polynucleotide. The expression cassettes can be used to transcribe RNA molecules that inhibit endogenous CV expression or to encode CV polypeptides that enhance CV activity in the host cell.

In the case where the inserted CV polynucleotide sequence is transcribed and translated to produce a functional CV polypeptide, one of skill will recognize that because of codon degeneracy, a number of polynucleotide sequences will encode the same polypeptide. These variants are specifically covered by the term "CV polynucleotide". In addition, the term specifically includes sequences (e.g., full length sequences) substantially identical (determined as described below) with a CV gene sequence encoding a CV polypeptide of the invention.

In the case of polynucleotides used to express CV RNA molecules that inhibit expression of an endogenous CV gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman, *Add. APL. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. U.S.A.* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned polynucleotide or polypeptide sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide or polypeptide sequences means that a polynucleotide or polypeptide comprises a sequence that has at least 85% sequence identity to a reference polynucleotide or polypeptide sequence. In the case of CV polypeptides of the invention, the reference polypeptide sequence can be any one of SEQ ID NOs: 2, 4, 6, 8, 10, 12, 14, 16, 18, 20, 22, 24, 26, 28, 30, 32, 34, 36, 38, 40, 42, or 44. In the case of CV polynucleotides of the invention, the reference polynucleotide sequence can be any one of SEQ ID NOs: 1, 3, 5, 7, 9, 11, 13, 15, 17, 19, 21, 23, 25, 27, 29, 31, 33, 35, 37, 39, 41, or 43. More preferred embodiments include CV polypeptides or polynucleotides at least 90%, 95%, or 99% compared to a reference sequence (e.g., any one of SEQ ID NOs: 2, 4, 6, 8, 10, 12, 14, 16, 18, 20, 22, 24, 26, 28, 30, 32, 34, 36, 38, 40, 42, or 44, or any one of SEQ ID NOs: 1, 3, 5, 7, 9, 11, 13, 15, 17, 19, 21, 23, 25, 27, 29, 31, 33, 35, 37, 39, 41, or 43) using the programs described herein; preferably BLAST using standard parameters, as described below. Accordingly, polynucleotide sequences encoding a CV polypeptide used in the methods of the present invention include nucleic acid sequences that have substantial identity to the sequences disclosed here. One of skill will recognize that these values can be appropriately adjusted to determine corresponding identity of proteins encoded by two nucleotide sequences by taking into account codon degeneracy, amino acid similarity, reading frame positioning and the like. CV polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that two CV nucleotide sequences are substantially identical is if the two molecules hybridize to each other, or a reference CV polynucleotide (e.g, any one of SEQ ID NOs: 1, 3, 5, 7, 9, 11, 13, 15, 17, 19, 21, 23, 25, 27, 29, 31, 33, 35, 37, 39, 41, or 43) under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

DETAILED DESCRIPTION OF THE INVENTION

Figure 1:
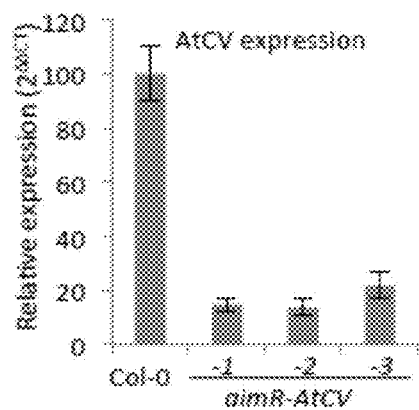
FIG. 1 shows that artificial miRNA silencing of AtCV delayed the chloroplast degradation induced by salt stress. (A) Quantitative RT-PCR analysis of AtCV expression in all leaves from 30-day-old plants of Col-0 and three independent artificial-microRNA-silenced lines of AtCV (amiR-1, amiR-2 and amiR-3). (B) leaf chlorophyll content of Col-0 and three independent AtCV-silenced lines (amiR-1,-2,-3) during salt stress treatment (50 mM NaCl for 3 days, 100 mM NaCl for 3 days, 150 mM NaCl for 10 days). Chlorophyll was extracted from leaf tissues. Mean±SD values were obtained from three independent experiments. Asterisk indicates P<0.001.
Figure 1:
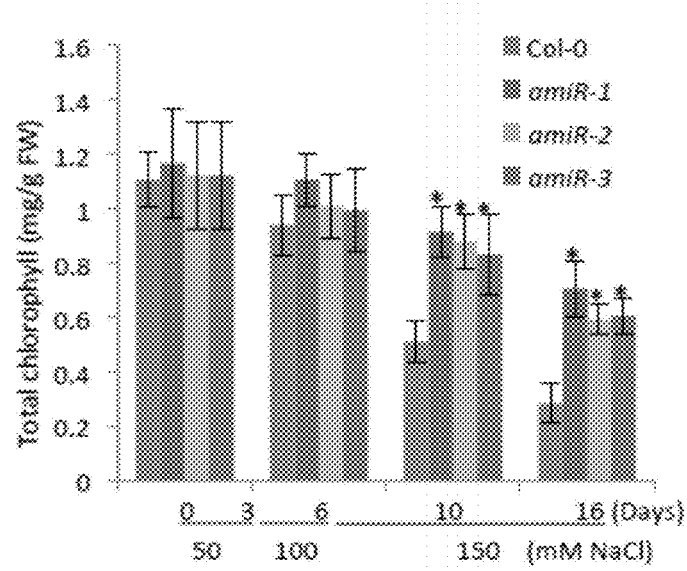

The invention is based at least in part on the discovery that modulation of CV expression and activity in plants can be used to confer desirable traits on plants. As shown below, CV proteins are associated with stress-induced chloroplast degradation. Thus, inhibiting expression or activity of the protein will inhibit or delay stress-induced chloroplast degradation and will confer tolerance to a variety of stress conditions. Alternatively, enhancing CV expression or activity will promote chloroplast degradation and will enhance nutrient assimilation in desired sink tissues, such as young leaves, fruit, or seeds.

Thus, in some embodiments, the present invention provides plants (which can be transgenic or non-transgenic) in which expression of the endogenous CV gene is inhibited. Such plants are more tolerant to a stress condition (abiotic or biotic) than a corresponding control or reference plant. As used herein, the term "tolerant" when used in reference to a stress condition of a plant, means that the particular plant, when exposed to a stress condition, shows less of an effect, or no effect, in response to the condition as compared to a corresponding control or reference plant (i.e., a naturally occurring wild-type plant or a plant not containing a construct of the present invention). As a consequence, a plant of the present invention shows improved agronomic performance (such as increased biomass, higher yields, and/or more seed production) as a result of enhanced abiotic or biotic stress tolerance and grows better under more widely varying conditions. Preferably, the plant is capable of substantially normal growth under environmental conditions where the corresponding control or reference plant shows reduced growth, yield, metabolism or viability, or increased male or female sterility.

A plant's response to abiotic stress includes the production of excess reactive oxygen species (ROS), including singlet oxygen, superoxide, hydrogen peroxide and hydroxyls radicals, which act as signaling molecules and play a role in the initiation of defense mechanisms. ROS are involved in wide variety of environmental stresses in plants. Excessive temperature extremes, water stress, ion imbalances due to salinity, air pollution, and mechanical damage lead to chemical signals propagated through ROS. Adaptation to the stress involves quenching of ROS signal through one or more anti-oxidant enzymes or compounds, such as superoxide dismutase (SOD), glutathione, ascorbate, carotenoids, and others. When the plant's quenching systems are exceeded by the environmental stress, extensive and rapid degeneration reactions can occur through ROS, such as protein denaturation and lipid peroxidation. Thus, one of skill will recognize that improved tolerance to one particular type of abiotic stress, such as drought or salt, can be indicative of a similarly improved tolerance to other types of abiotic stress.

In other embodiments, the invention provides plants in which CV expression and/or activity is enhanced and which have enhanced nutrient assimilation in desired sink tissues in the plant. Within a plant, a "source" may be defined as a tissue or organ (usually a photosynthetic tissue or organ, such as a leaf) which exports sugars and other nutrients to a "sink" tissue (usually a storage root, tuber, fruit seed, or young organ). As discussed above, during senescence, source tissues are the site of the degradation of chloroplast proteins through the activation of various chloroplast proteases. The protease products are then mobilized into vesicles via extensive vesicular trafficking to young tissues (sinks), where nitrogen and other nutrients are used for biosynthetic processes. Thus, plants having enhanced CV expression and/or activity provide more nutrients to sink tissues such as storage roots, tubers, young organs, fruits and seeds.

For example in a typical embodiment, an expression cassette comprising a CV polynucleotide operably linked to a chemically induced promoter is introduced into a desired plant (e.g., a tomato plant). At the time of fruit set, the plant is treated with a chemical that induces expression of the CV polynucleotide to induce chloroplast degradation in desired tissues in the plant (e.g., leaves adjacent to the fruit). Nitrogen and other nutrients resulting from the degradation of chloroplasts in the leaves are then assimilated by the fruit, thereby enhancing the nutritional content of the fruit.

As demonstrated below, CV proteins are highly conserved in the plant kingdom. Thus, one of skill will recognize the CV genes and proteins from a wide variety of plants can be used in the present invention. The proteins can be identified by the presence of the consensus sequence as shown here. In particular, a CV protein can be identified by the presence of either or both of the following consensus sequences: RxCxxWxxN (SEQ ID NO: 45) or ExxxPENLPRxxxxxR (SEQ ID NO: 46), where "x" can be any amino acid.

The invention has use over a broad range of plants, including species from the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Populus, Pyrus, Prunus, Raphanus, Secale, Senecio, Sinapis, Solanum, Sorghum, Theobroma, Trigonella, Triticum, Vitis, Vigna,* and *Zea.*

CV Polynucleotides and Expression Cassettes

The present invention provides isolated nucleic acid molecules comprising a CV polynucleotide of the present invention. The polynucleotide can be, for example, a DNA molecule that encodes a CV polypeptide or an RNA molecule that inhibits endogenous CV expression in a cell.

The isolated nucleic acids of the present invention can be made using standard recombinant methods, synthetic techniques, combinations thereof, or any method known to those of skill in the art.

The isolated nucleic acid compositions of this invention can be obtained from plant biological sources (e.g., tissues from the plant) or can be prepared by direct chemical synthesis using any number of methodologies familiar to those of skill in the art. In some embodiments, oligonucleotide probes that selectively hybridize under stringent conditions to the polynucleotides of the present invention are used to identify the desired CV sequence in a cDNA or genomic DNA library. Isolation of RNA and construction of cDNA and genomic libraries is well known to those of ordinary skill in the art.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

The present invention also provides recombinant expression cassettes comprising a CV polynucleotide. Such plant expression cassettes typically contain the CV polynucleotide operably linked to a promoter (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. For example, a cDNA or a genomic sequence encoding a full length a CV polypeptide, can be used to construct a recombinant expression cassette, which can be used to produce a CV protein in a desired host cell. Alternatively, the expression cassette may encode an RNA molecule that inhibits expression of an endogenous CV gene in the host cell. A recombinant expression cassette will typically comprise a polynucleotide of the present invention operably linked to transcriptional initiation regulatory sequences, which will direct the transcription of the polynucleotide in the intended host cell, such as tissues of a transformed plant.

A number of promoters can be used in the practice of the invention. A plant promoter fragment can be employed which will direct expression of the CV polynucleotide in all tissues of a regenerated plant. Such promoters are referred to herein as "constitutive" promoters and are active under most environmental conditions and state of development or cell differentiation. Examples of constitutive promoters include the cauliflower mosaic virus (CaMV) 35S transcription initiation region.

Alternatively, the plant promoter can direct expression of the polynucleotide under environmental control. Such promoters are referred to here as "inducible" promoters. Environmental conditions that may affect transcription by inducible promoters include biotic stress, abiotic stress, saline stress, drought stress, pathogen attack, anaerobic conditions, cold stress, heat stress, hypoxia stress, or the presence of light.

In addition, chemically inducible promoters can be used. Examples include those that are induced by benzyl sulfonamide, tetracycline, abscisic acid, dexamethasone, ethanol or cyclohexenol.

Examples of promoters under developmental control include promoters that initiate transcription only, or preferentially, in certain tissues such as leaves, roots, fruit, seeds, or flowers. These promoters are sometimes called tissue-preferred promoters. The operation of a promoter may also vary depending on its location in the genome. Thus, a developmentally regulated promoter may become fully or partially constitutive in certain locations. A developmentally regulated promoter can also be modified, if necessary, for weak expression.

As noted above, the invention provides a method of suppressing CV expression or activity in a plant using expression cassettes that transcribe CV RNA molecules that inhibit endogenous CV expression or activity in a plant cell. Suppressing or silencing gene function refers generally to the suppression of levels of CV mRNA or CV protein expressed by the endogenous CV gene and/or the level of the CV protein functionality in a cell. The terms do not specify mechanism and could include RNAi (e.g., short interfering RNA (siRNA) and micro RNA (miRNA)), anti-sense, cosuppression, viral-suppression, hairpin suppression, stem-loop suppression, CRSIPR, and the like.

A number of methods can be used to suppress or silence gene expression in a plant. The ability to suppress gene function in a variety of organisms, including plants, using double stranded RNA is well known. Expression cassettes encoding RNAi typically comprise a polynucleotide sequence at least substantially identical to the target gene linked to a complementary polynucleotide sequence. The sequence and its complement are often connected through a linker sequence that allows the transcribed RNA molecule to fold over such that the two sequences hybridize to each other.

RNAi (e.g., siRNA, miRNA) appears to function by base-pairing to complementary RNA or DNA target sequences. When bound to RNA, the inhibitory RNA molecules trigger either RNA cleavage or translational inhibition of the target sequence. When bound to DNA target sequences, it is thought that inhibitory RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides in length that are processed from longer precursor transcripts that form stable hairpin structures.

In addition, antisense technology can be conveniently used. To accomplish this, a nucleic acid segment at least substantially identical to the desired gene is cloned and operably linked to a promoter such that the antisense strand of RNA will be transcribed. The expression cassette is then transformed into a plant and the antisense strand of RNA is produced. In plant cells, it has been suggested that antisense RNA inhibits gene expression by preventing the accumulation of mRNA which encodes the protein of interest.

Another method of suppression is sense suppression. Introduction of expression cassettes in which a nucleic acid is configured in the sense orientation with respect to the promoter has been shown to be an effective means by which to block the transcription of target genes.

For these techniques, the introduced sequence in the expression cassette need not have absolute identity to the target gene. In addition, the sequence need not be full length, relative to either the primary transcription product or fully processed mRNA. One of skill in the art will also recognize that using these technologies families of genes can be suppressed with a transcript. For instance, if a transcript is designed to have a sequence that is conserved among a family of genes, then multiple members of a gene family can be suppressed. Conversely, if the goal is to only suppress one member of a homologous gene family, then the transcript should be targeted to sequences with the most variance between family members.

Gene expression can also be inactivated using recombinant DNA techniques by transforming plant cells with constructs comprising transposons or T-DNA sequences. Mutants prepared by these methods are identified according to standard techniques. For instance, mutants can be detected by PCR or by detecting the presence or absence of CV mRNA, e.g., by northern blots or reverse transcriptase PCR (RT-PCR).

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is well known.

Plant Transformation

Once an expression cassette comprising a CV polynucleotide of the present invention has been constructed, any technique known to those skilled in the art may be used to introduce the expression cassette into a plant.

Methods for transformation and regeneration of plants are well known in the art, and the selection of the most appropriate transformation technique for a particular embodiment of the invention may be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence.

Following transformation, cells or plants can be selected using a dominant selectable marker incorporated into the transformation vector. Typically, such a marker will confer antibiotic or herbicide resistance on the transformed cells or plants, and selection of transformants can be accomplished by exposing the cells or plants to appropriate concentrations of the antibiotic or herbicide.

Transformed cells may be regenerated into plants in accordance with techniques well known to those of skill in the art. The regenerated plants may then be grown, and crossed with the same or different plant varieties using traditional breeding techniques to produce desired plants. Two or more generations may be grown to ensure that the desired phenotype (e.g., stress tolerance) is stably maintained and inherited and then seeds harvested to ensure the desired phenotype or other property has been achieved.

In some embodiments, the methods of the invention include a step of selecting plants with the desired traits. The plants made by the methods of the invention can be screened by well-known techniques, depending on the desired trait. The determination that a plant modified according to a method of the invention has enhanced nutrient assimilation in desired tissues (e.g., fruit or seeds) can be made by comparing yield of a modified plant with yield of a control (reference) plant that has not been modified. A plant of the invention may show increase in yield of at least about 110%, preferably at least about 150%, more preferably at least about 200%, as compared to a corresponding unmodified reference plant.

Plants showing enhanced stress tolerance can be selected according to the particular stress condition. For example, a plant having increased salt tolerance can be identified by growing the plant on a medium such as soil that contains salt at a level more than about 100% of the amount of salt in the medium on which the corresponding reference plant is capable of growing. Advantageously, a plant treated according to a method of the invention can grow on a medium or soil containing salt at a level of at least about 110%, preferably at least about 150%, more preferably at least about 200%, and optimally at least about 400% of the level of salt in the medium or soil on which a corresponding reference plant can grow.

Drought-tolerance can be determined by any of a number of standard measures including turgor pressure, growth, yield, and the like. For example, a plant having increased tolerance to drought can be identified by growing the plant under conditions in which less than the optimal amount of water is provided to the plant through precipitation and/or irrigation. Particularly, a plant having increased tolerance to drought can be identified by growing the plant on a medium such as soil that contains less water than the medium on which the corresponding reference plant is capable of growing. Advantageously, a plant treated according to a method of the invention can grow on a medium or soil containing water at a level of less than about 90%, preferably less than about 80%, more preferably less than about 50%, and optimally less than about 20% of the amount of water in the medium or soil on which a corresponding reference plant can grow. Alternatively, a plant having increased tolerance to drought can be identified by its ability to recover from drought (little or no applied water) when rehydration is provided after a period of drought. Advantageously, a plant treated according to a method of the invention can recover when rehydration is provided after a period of at least 3 days drought, at least 5 days drought, preferably at least 7 days drought, more preferably at least about 10 days drought, and optimally at least about 18 days drought.

Water use efficiency can be determined by evaluating the amount of dry biomass that a plant accumulates (which can be vegetative, reproductive, or both, depending on the yield component(s) of interest) per unit water available to the plant. A plant having enhanced water use efficiency will have a greater amount of dry biomass accumulation per unit water available than the corresponding reference plant grown under the same conditions. Water use efficiency at the leaf or plant scale refers to the ratio between the net $CO_2$ assimilation rate and the transpiration rate, usually measured over a period of seconds or minutes. A plant with enhanced water use efficiency will have higher yields (such as 1-5%, 5-10%, 10-15% higher) under restricted water conditions compared to the corresponding reference plant grown under the same conditions.

Heat tolerance can be determined by evaluating the amount of dry biomass that a plant accumulates (which can be vegetative, reproductive, or both, depending on the yield component(s) of interest) relative to increasing temperatures. A plant having enhanced heat tolerance will have higher yields (such as 1-5%, 5-10%, 10-15% higher) under increased temperature conditions (such as 1° C., 2° C., 3° C., 4° C., etc.) compared to the corresponding reference plant grown under the same conditions.

Once the appropriate selections are made, the process is repeated. The process of backcrossing to the recurrent parent and selecting for the desired trait is repeated for a number of generations. The last backcross generation can then be selfed in order to provide for homozygous pure breeding progeny.

Methods of Making Nontransgenic Plants

A number of means are available for knocking out or inactivating an endogenous CV gene without using recombinant techniques. Thus, the plants produced by these methods are not transgenic.

Methods for introducing genetic mutations into plant genes and selecting plants with desired traits are well known. For instance, seeds or other plant material can be treated with a mutagenic chemical substance, according to standard techniques. Such chemical substances include, diethyl sulfate, ethylene imine, ethyl methanesulfonate (EMS) and N-nitroso-N-ethylurea. Alternatively, ionizing radiation from sources such as, X-rays or gamma rays can be used.

The resulting mutant plants can then be selected for mutations in the CV gene by a number of methods. For example, TILLING (Targeting Induced Local Lesions IN Genomics) can be used to select plants in which the CV gene is knocked out. (See, e.g., McCallum et al., (2000), *Plant Physiol* 123:439-442; McCallum et al., (2000)*Nat Biotechnol* 18:455-457; and, Colbert et al., (2001) *Plant Physiol* 126:480-484.

TILLING combines introduction of high density point mutations with rapid detection of the mutations. Any mutagen (e.g., EMS) can be used to mutagenize plant seed. The mutant plants are then self-fertilized and the resultant plants are then screened for mutation in the CV gene and/or for specific phenotypes. In a typical procedure, DNA from mutagenized plants is pooled and mutations in a CV gene are detected by detection of heteroduplex formation. To do this, the CV gene in each pooled sample is amplified (e.g., by PCR) and then denatured and annealed to allow formation of heteroduplexes, which indicate the presence of one or more point mutations in the CV gene. Heteroduplexes can be identified by Denaturing High Performance Liquid Chromatography (DPHPLC). Typically, chromatography is performed while heating the DNA. Heteroduplexes have lower thermal stability, resulting in faster movement in the chromatography column. As a result, the pools that carry a mutation in a CV gene are identified. Individual DNA from plants that make up the selected pooled population can then be identified and sequenced.

Other methods for detecting mutations in a CV gene include constant denaturant capillary electrophoresis and single-stranded conformational polymorphism. Heteroduplexes can also be detected by using mismatch repair enzymology. See Colbert et al., (2001) *Plant Physiol* 126: 480-484.

Mutations in CV genes can also be introduced in a site-specific manner by artificial zinc finger nuclease (ZFN), TAL effector (TALEN) or CRISPR/Cas technologies as known in the art. CRISPR (Clustered Regularly Interspaced Short Palindromic Repeats)/Cas (CRISPR-associated) systems, are adaptive defense systems in prokaryotic organisms that cleave foreign DNA. In the typical system, a Cas9 RNA-guided endonuclease is guided to a desired site in the genome using customizable small RNAs that target sequence-specific single- or double-stranded DNA sequences. The CRISP/Cas system has been used to induce site specific mutations in plants (see Miao et al. (2013) *Cell Research* 23:1233-1236).

The non-transgenic plants made by any of the above methods can be selected for the desired stress tolerance trait (e.g., drought tolerance, salt tolerance, and the like) using any of the selection methods described above.

EXAMPLES

The following examples are offered to illustrate, but not to limit the claimed invention.

Example 1

Methods

Plant Materials and Growth Conditions

*Arabidopsis thaliana* (Col-0) plants were grown in a growth chamber at 23° C. under a 16 h light/8 h dark regime. MS/2 media (0.5% sucrose, pH5.7) were used for plate-grown plants. Transgenic *Arabidopsis* plants expressing stroma-targeted DsRed (CT-DsRed) were generated as described previously (Ishida et al. 2008, Plant Physiol 148: 142-155). The generation of transgenic plant GTP-ATG8a (Thompson et al. 2005, Plant Physiology 138: 2097-2110), the vacuole marker line VAMP711-RFP (Uemura et al. 2004, Cell Structure And Function 29: 49-65), and the plastoglobule marker line PGL34-YFP (Vidi et al. 2007, BMC Biotechnol 7) were performed as described previously.

All the constructs in this study were generated using the Gateway system (Invitrogen, Grand Island, N.Y.). cDNA of AtCV (At2G25625) was amplified from mature leaf cDNA of Col-0. The 3'-terminus of AtCV gene was fused with GFP by fusion PCR and a linker (GGAAGGAA) was introduced between AtCV and GFP. The single AtCV gene and the fusion fragment (AtCV-linker-GFP) were both cloned into pDONR207 by BP reactions. The pDONR207-AtCV was recombined via LR reactions into destination vectors: pEarley-Gate 101 (Earley et al. 2006 Plant Journal 45: 616-629) for YFP fusion (AtCV-YFP), pB7RWG2 (https://gateway-.psb.ugent.be/search) for RFP fusion (AtCV-RFP), and a chemicalinducible system pBAV154 (Vinatzer et al. 2006, Mol Microbiol 62: 26-44) for stable transformation (DEX: AtCVHA). The pDONR207-AtCV-linker-GFP was recombined into pEarley-Gate 100 for transient expression (AtCV-GFP) and chemical-inducible system pBAV154 for stable transformation (DEX:AtCV-GFP), respectively. An artificial miRNA (TTACACGTAATGAACTTCCAG, SEQ ID NO: 47) targeting AtCV (amiR-AtCV) was designed with WMD3 (http://wmd3.weigelworld.org/cgi-bin/webapp.cgi) and cloned (Schwab et al. 2006, Plant Cell 18: 1121-1133) into pEarley—Gate 100 for stable transformation. Using the same strategy, the genes of AtPsbO1 (At5G66570), AtCYP20-2 (At5G13120), and FtsH1 (At1G50250) were fused with CFP first and then recombined into pEarley-Gate 100 to obtain constructs PsbO1-CFP, CYP20-2-CFP, and FtsH1-CFP, respectively. Meanwhile, the deletion mutagenesis of chloroplast transit signal peptide (M1-L22) and C-terminus conserved domain (R92-V152) was performed by PCR and the mutation fragment were fused with GFP and recombined into pEarley-Gate 100 to generate constructs AtCVΔCGFP and AtCVΔN-GFP. The transient expressions were performed in cotyledons of Col-0 young seedlings, as described previously (Marion et al. 2008, The Plant Journal: For Cell And Molecular Biology 56: 169-179). The stable transformation was performed according to the floral dipping method (Clough and Bent 1998, Plant Journal 16: 735-743).

RNA Extraction and Quantitative RT-PCR

For assessing senescence-induced AtCV expression, total RNA was extracted from cassette leaf 7 of Col-0 plants growing in soil under 16 h light/8 h dark. For testing abiotic stress-induced AtCV expression, total RNA was extracted from all the leaves of 10-dayold seedlings growing without (control) or with 100 mM NaCl or 2 μM methyl viologen (MV) for 2 days. For assessing artificial miRNA silencing of AtCV, the cassette leaf 7 from 30-day-old plants of Col-0 and amiR-AtCV lines were used for total RNA extraction. Total RNA was extracted by using RNeasy Mini Kit (Qiagen, Redwood City, Calif.) with three biological replicates. First-strand cDNA was synthesized from 1 μg of total RNA with QuantiTech reverse transcription kit (Qiagen). qPCR was performed on the StepOnePlus (Applied Biosystems, Grand Island, N.Y.) using SYBR GREEN (Bio-Rad, Hercules, Calif.). The 2-AACT method (Livak and Schmittgen 2001, Methods 25: 402-408) was used to normalize and determine the mRNA level relative to an internal reference gene, TIP41-like family protein.

Fluorescence and Confocal Microscopy

Fluorescence microscopy was performed using an Inverted Zeiss LSM 710 confocal laser scanning microscope (Carl Zeiss AG) equipped with a X40 water immersion objective. For GFP, the excitation wavelength was 488 nm and emission was 500-530 nm, CFP (440 nm/460-490 nm), YFP (514 nm/525-552 nm), DsRed (543 nm/575-625 nm), lysotracker Red (561 nm/570-600 nm), RFP (561 nm/600-660 nm), and Chlorophyll (633 nm/650-720 nm). To avoid crosstalk between the fluorescence channels, sequential scanning was used when necessary. Images were processed by ImageJ (rsbweb.nih.gov/ij/) and assembled by Photoshop software (Adobe).

Immunolabeling Transmission Electron Microscopy

The 10-day-old seedlings of DEX:AtCV-GFP transgenic plants and Col-0 were cultured in liquid MS/2 media containing 10 μM DEX for 20 h. The cotyledons were observed by confocal microscope and the tissues with high expression of AtCV-GFP were fixed in paraformaldehyde (2%) and glutaraldehyde (2.5%) as previously described (Shipman and Inoue 2009, Febs Letters 583: 938-942). Immunolabeling was performed on ultrathin sections on Formva-coated grids using anti-GFP antibody (Novus Biologicals, Littleton, Co) and goat anti-rabbit secondary antibody conjugated with 10 nm gold (Brithish BioCell International Ltd, Cardiff, South Glamorgan, United Kingdom). All the grids were stained with uranyl acetate and lead citrate before being observed on a Phillips CM120 Biotwin. Images were taken with a Gatan MegaScan digital camera (model 794/20). For the double immunolabeling experiments, leaf sections from the transgenic line DEX:AtCV-HA (DEX-3) were blotted with anti-HA antibody (from mouse) and anti-PsbO (from rabbit), then treated subsequently with 5 nm gold-conjugated goat anti-mouse IgG and 20 nm gold-conjugated goat anti-rabbit IgG for 1 h. The grids were stained with uranyl acetate and lead citrate for observation.

Immunoblotting Analyses

Plant leaf tissues were weighed, frozen in liquid N2, and ground in three volumes of 2× Laemmli sample buffer. Total proteins were separated by SDS-PAGE and transferred to PVDF membrane (Bio-Rad, Hercules, Calif., USA) and probed as previously described (Wang et al. 2011, Plant Cell 23: 3412-3427). Monoclonal antibodies raised against HA tag were purchased from Covance (Princeton, N.J., USA) (#MMS-101P). Antibodies raised against PsbO (#AS05092), sucrose phosphate synthase/SPS (#AS03035A), PsbA (#AS06166A), PsbA/D1 (#AS01016), GS1/GS2 or GLN1/GLN2 (AS08295), and Lhcb2 (#AS01003) were obtained from Agrisera (Vannas, Sweden). Horseradish peroxidase-conjugated secondary antibodies were purchased from Santa Crus Biotechnology (Dallas, Tex., USA).

Immunoprecipitation and Liquid Chromatography-Tandem Mass Spectrometry (LCMS/MS)

Four-day-old seedlings of Col-0 and transgenic plants DEX:AtCV-HA-3 (DEX-3) were cultured in MS/2 media containing 10 μM DEX for 4 days and then kept in the dark for additional 2 days. The shoots of plants were harvested, ground in liquid N2 and incubated at 4° C. for 3 h with lysis buffer provided by μMACS HA Isolation Kit (Miltenyl Biotec, San Diego, Calif., USA), containing Protease Inhibitor Cocktail (Sigma-Aldrich, St. Louis, Mo., USA). Co-immunoprecipitation was performed using anti-HA magnetic beads from μMACS HA Isolation Kit (Miltenyl Biotec, San Diego, Calif., USA) and incubating the cell lysis with beads at 4° C. for 2 h. LC-MS/MS analysis was performed in Genome Center of University California, Davis, as described previously (Shipman-Roston et al. 2010, Plant Physiol 152: 1297-1308). Scaffold (version Scaffold 3) was used to validate MS/MS-based peptide and protein identification. Peptide identifications were accepted if they could be established at >80.0% probability. Protein identifications were accepted if they could be established at >95.0% probability and contained at least three identified peptides.

For immunoprecipitation of the PsbO protein, the seedlings of Col-0, transgenic plant DEX:AtCV-HA-3 and DEX::AtCVΔC-HA were treated with DEX by the above-mentioned procedures. Cell lysis was incubated with anti-PsbO antibody and magnetic Dynabeads Protein A (Life Technologies™, Grand Island, N.Y., USA) for 2 h at 4.0 and immunoprecipitated samples were checked by immunoblotting with anti-PsbO and anti-HA antibody, respectively.

Bimolecular Fluorescence Complementation

The four vectors pDEST-GWVYNE, pDEST-VYNE(R)GW, pDEST-GWSCYCE, and pDESTSCYCE(R)GW from the GATEWAY-based BiFC vector systems (Gehl et al. 2009, Mol Plant 2: 1051-1058) were employed to fuse AtCV, PsbO1 and SGR1 (At4G22920) with N-terminus of yellow fluorescent protein Venus (VenusN) and C-terminus of super cyan fluorescent protein (SCFPC), respectively, to obtain the constructs AtCV-SCFPC, VenusN-AtCV, PsbO1-VenusN, SCFPC-PsbO1, SGR1-VenusN, and AtCVAC-SCFPC. All the constructs were introduced into *A. tumefaciens* strain GV3101. The transient expression was performed in cotyledons of Col-0 young seedlings, as described previously (Marion et al. 2008, The Plant Journal: For Cell And Molecular Biology 56: 169-179).

GUS Staining and Chlorophyll Measurement

For GUS staining, the whole seedlings were submerged in standard X-GlcA solution (50 mM sodium phosphate buffer pH7.0, 10 mM EDTA, 0.1% Triton X-100, and 0.5 mg/mL X-GlcA) and vacuum infiltrated for 5 min. Incubate at 37° C. for 16 h to develop blue color, as described previously (Jefferson et al. 1987, Plant Journal 52: 197-209).

For chlorophyll measurements, the leaves were weighted and ground in liquid N2. The chlorophyll was extracted in 80% acetone and the absorbance (A) at 663 nm and 645 nm was measured using spectrophotometry (DU-640, Beckman Coulter, Brea, Calif., USA). Total chlorophyll contents were calculated as described elsewhere (Porra 2002, Photosynth Res 73: 149-156).

Results

AtCV Expression was Activated by Abiotic Stress and Senescence but Suppressed by Cytokinin During abiotic stress, the breakdown of the plant photosynthetic machinery is a major factor in the reduction of CO2-assimilation by plants (Tambussi et al. 2000, Physiologia Plantarum 108: 398-404). It has been shown previously that the cytokinin-dependent inhibition of drought-induced senescence resulted in sustained photosynthetic activity during the stress episode and enhanced tolerance to water deficit (Rivero et al. 2007, Proceedings of the National Academy of Sciences of the United States of America 104: 19631-19636; Rivero et al. 2009, Plant Physiology 150: 1530-1540; Rivero et al. 2010, Plant and Cell Physiology 51: 1929-1941). The expression of isopentenyl synthase (IPT), encoding a key enzyme in cytokinin synthesis, under the control of a maturation- and stress-induced promoter (pSARK) leads to the protection of the photosynthetic apparatus and enhanced chloroplast stability (Rivero et al. 2010; Reguera et al. 2013, Plant Physiology 163: 1609-1622). Using DNA microarrays, we analyzed RNA expression patterns in wild-type and transgenic pSARK::IPT rice plants during water deficit (Peleg et al. 2011, Plant Biotechnology Journal 9: 747-758; Reguera et al. 2013, Plant Physiology 163: 1609-1622). The expression of one gene encoding a chloroplast protein with unknown function (LOC_Os05g49940) was activated by stress in the wildtype plants but not in the transgenic pSARK:IPT plants (Peleg et al., 2011, Plant Biotechnology Journal 9: 747-758).

The Arabidopsis genome contains At2g25625, a gene homologue to LOC_Os05g49940, whose function remains to be characterized. The public microarray database (Winter et al. 2007, Plos One 2: e718) indicated that At2g25625 expression was hardly detectable in young tissues, but its expression was greatly induced by abiotic stress and senescence when a massive chloroplast degradation occurred (Hortensteiner 2006, Annual Review of Plant Biology 57: 55-77; Martinez et al. 2008, Annual Review Of Plant Biology 61: 443-462). Therefore, we surmised that the gene could play role(s) in chloroplast destabilization.

The gene in Arabidopsis (At2G25625) was cloned and termed AtCV (Chloroplast Vesiculation) due to the subcellular localization of the encoded protein and its functions as revealed in this study. As indicated by quantitative RT-PCR assays (FIGS. 1A and 1B), AtCV expression was activated by senescence and abiotic stresses such as salt stress and methyl viologen (MV)-induced oxidative stress. AtCV expression was significantly down-regulated by 3 h treatment with cytokinin, a phytohormone delaying senescence (Gan and Amasino 1995, Science 270: 1986-1988). To study the tissue specific expression of AtCV, we cloned the AtCV gene's native promoter, consisting of a 2 kb upstream region before the start codon, and used it to drive the reporter gene β-glucuronidase (GUS). The GUS staining assays of transgenic plants ProAtCV:GUS suggested that AtCV gene was expressed strongly in senescent and mature leaves but not in young leaves of 40-day-old plant. In leaves from 21-day-old seedlings, AtCV expression was hardly detectable but its expression was substantially enhanced by salt stress treatment.

AtCV Targets Chloroplasts and Induces the Vesicle Formation in Chloroplasts.

AtCV is predicted to contain a chloroplast transit signal peptide at the N terminus by the ChloroP 1.1 Server (www.cbs.dtu.dk/services/ChloroP/). In order to assess AtCV subcellular localization, we fused the enhanced green fluorescence protein (GFP) to the C-terminus of AtCV. The fusion gene AtCV-GFP was transiently expressed in cotyledons of Arabidopsis plants constitutively expressing stroma-targeted DsRed (CT-DsRed) (Ishida et al. 2008). The confocal microscopy observations indicated that AtCV-GFP localized in chloroplasts and concentrated in some vesicle-like spots. The AtCV-containing vesicles (CCVs) also aggregated outside of the chloroplast in some unknown compartments that included the stroma-targeted DsRed but not chlorophyll. Interestingly, AtCV-GFP localized in both the cytosol and chloroplasts in epidermal cells. The expression of GFP alone resulted in a green fluorescence signal not associated with chloroplasts. In addition, the movement of CCV departing from chloroplasts was captured by timelapse observation of confocal microscope.

The chloroplast localization of AtCV was further assessed by immunolabeling using antibodies raised against GFP. The immunolabeled gold particles were mostly associated with thylakoids or envelope membranes rather than stroma before the formation of vesicles. AtCV's membrane association can be explained by its predicted transmembrane domain (aramemnon.botanik.uni-koeln.de). In some AtCV-labeled chloroplasts, the envelope membrane lost integrity and thylakoid membranes appeared swelled and unstacked. CCVs were observed attached to the envelope membrane of disassembled chloroplasts or protruding from the unstacked thylakoid membranes. The detection of GFP by immune-labelling TEM in cotyledon mesophyll cells of DEX:AtCV-GFP transgenic plants showed that 87% of the gold particles were localized in chloroplasts and CCVs. In addition, we used leaf sections from transgenic plants DEX:AtCV-HA (DEX-3) for the doubleimmunolabeling with anti-HA and anti-PsbO antibodies. The results showed that the CCVs that are close to, but not associated with, broken chloroplasts could also be labeled by antibodies raised against PsbO, a subunit of photosystem II complex localized in thylakoid membrane. Moreover, CCVs also contained Tic20-II, a protein from chloroplast inner envelope membranes (Machettira et al. 2011, Plant Mol Biol 77: 381-390). These results suggested that CCVs generated from chloroplast membranes that were disrupted by AtCV. These vesicles and disrupted chloroplast structures were not seen in cotyledons from wild type seedlings.

AtCV-Containing Vesicles were Mobilized to the Vacuole Through a Pathway Independent of Autophagy and SAVs The role of autophagy in the mobilization of Rubisco and stroma proteins to the vacuole is well established (Ohsumi 2001, Nature Reviews Molecular Cell Biology 2: 211-216; Ishida et al. 2008, Plant Physiol 148: 142-155; Bassham 2009; Wada et al. 2009). During autophagy, cytosolic components and intact or partially broken organelles are engulfed in membrane-bound vesicles, called autophagosomes, that deliver the vesicle contents to the vacuole for degradation. We transiently expressed the AtCV-RFP fusion gene in cotyledons from transgenic plants expressing the autophagic marker GFP-ATG8a (Thompson et al. 2005, Plant Physiology 138: 2097-2110). The red fluorescence of AtCV-RFP did not overlap with the green fluorescence of GFP-ATG8a. Moreover, when AtCV-GFP was expressed in autophagy-defective mutants atg5-1 (Ishida et al. 2008), CCVs were observed both inside and outside of the chloroplasts, further suggesting that the formation and trafficking of CCVs were independent of autophagy.

During senescence, the formation of small acidic senescence associated vacuoles (SAV) aid in the degradation of chloroplast proteins. SAVs are formed through a pathway that is independent of autophagy (Otegui et al. 2005; Martinez et al. 2008 Plant Journal 56: 196-206; Carrion et al. 2013, J Exp Bot 64: 4967-4980). To rule out a possible relationship between CCVs and SAVs, we attempted staining cotyledons from plants expressing AtCV-GFP with Lysotracker Red, a fluorescent dye that stains acidic lytic vesicles including SAVs (Otegui et al., 2005, Plant Journal 41: 831-844). The lack of CCV staining by Lysotracker Red, indicated that CCV's milieu differed from that of SAVs. In addition, the transient co-expression of SAG12-RFP along with AtCV-GFP in cotyledon cells showed that the SAV marker SAG12-RFP did not colocalized with AtCV-GFP.

A Dexamethasone-(DEX)-induced promoter was used to express AtCV-GFP. DEX:AtCV-GFP stably transformed plants were treated with DEX and GFP fluorescence was monitored. Six hours after DEX treatment, AtCV-GFP was seen decorating mesophyll cell chloroplasts and stromules (stroma-filled tubules; Hanson and Sattarzadeh, 2008 Plant, Cell and Environment 31: 646-657, and references therein) extending from the chloroplasts. Eighteen hours following DEX treatment, the CCVs moved out from the chloroplast along with the stroma-targeted CT-DsRed. These observations were consistent with AtCV transient expression results. Similar results were observed in DEX-induced expression of AtCV-GFP in true leaf cells, and in cotyledon and hypocotyl cells. CCVs also could carry CT-DsRed out of chloroplasts and aggregate in cytosols of mesophyll cells of true leaves. To exclude the possibility that CCVs were produced at the ER, DEX:AtCV-GFP transgenic plants were treated with DEX for 17 hours and with Concanamycin A, an inhibitor of intracellular vesicle trafficking (Dettmer et al. 2006, Plant Cell 18: 715-730) for an additional hour. Concanamycin A treatment inhibited the release of CCVs from chloroplasts since the CCVs appeared adhered to the chloroplasts after treatment.

To assess whether CCVs were eventually transported to the vacuole, the AtCV-GFP was transiently expressed in stable report lines of Rab2a-RFP, a prevacuolar compartment rab5 GTPase Rhal (Foresti et al. 2010, Plant Cell 22: 3992-4008) and VAMP711-RFP, a tonoplast R-SNARE (Uemura et al. 2004, Cell Structure And Function 29: 49-65). Our results showed that AtCV-GFP overlapped with RabF2a-RFP and VAMP711-RFP in hypocotyls cells 3 days after transient expression, supporting the mobilization of CCVs to the central vacuole.

AtCV Overexpression Leads to Chloroplast Degradation

Attempts to overexpress AtCV under the control of the CaMV35S constitutive promoter were not successful, suggesting that the high AtCV expression could be lethal. We used an alternative approach utilizing a chemically-inducible expression system to drive the expression of the AtCV-HA fusion gene. The phenotypical analysis of three independent stable lines DEX-1, DEX-2, and DEX-3 showed that DEX-induced AtCV expression resulted in leaves chlorosis and growth retardation. The leaf chlorophyll contents under DEX treatment decreased as compared with that of untreated transgenic and wild-type plants. Western blot analyses revealed that the PSI complex subunit PsaB, PSII subunits (PsbO1 and D1) and stromal protein glutamine synthase 2 (GS2) were degraded in DEX-treated plants. The levels of cytosolic sucrose phosphate synthase (SPS) remained unchanged upon DEX treatment, whereas the abundance of cytosolic glutamine synthase 1 (GS1) increased, consistent with a previous study showing the up-regulation of GS1 expression during senescence (Bernhard and Matile 1994 Plant Sci 98: 7-14). Oxidative stress, induced by the exposure of the plants to 0.3 μM methyl viologen, enhanced stress-induced chloroplast degradation in transgenic plants expressing AtCV. Overexpression of AtCV-GFP also induced the accelerated senescence phenotype under 50 mM NaCl. These results indicated that the over-expression of AtCV lead to premature senescence and chloroplast degradation.

AtCV Silencing Lead to Delayed Chloroplast Degradation

Figure 2:
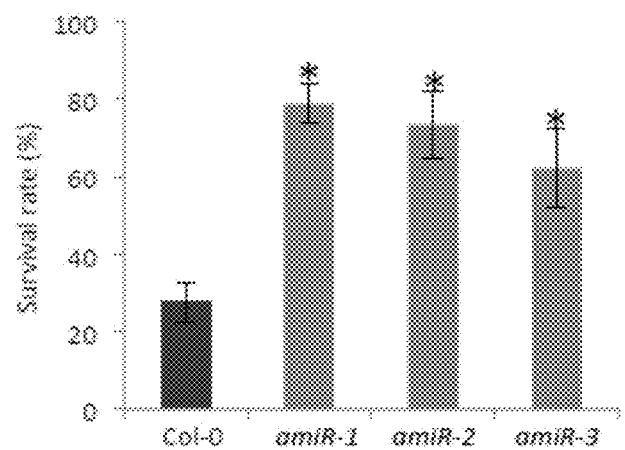
FIG. 2 shows that silencing AtCV increased drought tolerance in trangsenic plants. Plants of Wild type Col-0 and AtCV-silenced transgenic lines (amiR-1,-2 and-3) were subjected to water stress for 14 days and rewatering for 4 days. (A) Survival rate was determined 4 days after rewatering. 15 plants for each line were evaluated and Mean±SD were obtained from three independent experiments. Asterisk means P<0.001. (B) AtCV expression in leaves from Col-0 and amiR-1 plants during drought treatment were determined by quantitative PCR.
Figure 2:
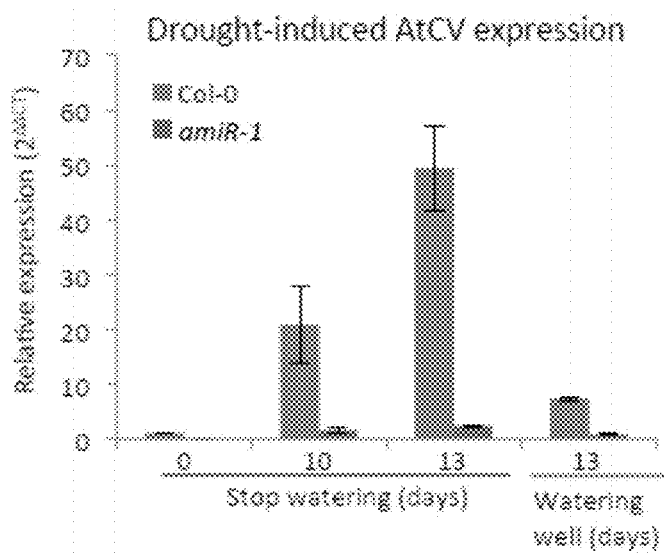

An amiRNA targeting AtCV (amiR-AtCV) was designed using WMD3 (wmd3.weigelworld.org/cgi-bin/webapp.cgi) (Schwab et al. 2006, Plant Cell 18: 1121-1133) and its expression was driven by the CaMV35S promoter. Three independent transgenic lines (amiR-AtCV1-3) were selected and AtCV silencing was examined by quantitative RTPCR (FIG. 1A). AtCV-silenced plants had no apparent developmental defects and their natural senescence was also indistinguishable from wild type plants. However, when 20-day-old seedlings of wild-type and amiR-AtCV plants were treated with gradually-increasing NaCl concentrations (FIG. 1B), the wild type plants displayed severe leaf senescence symptoms, while the amiR-AtCV plants remain green. Chlorophyll measurement of wild-type cassette leaves indicated decrease in chlorophyll contents during the treatment, while salt stress-induced leaf senescence was delayed in AtCV-silenced plants (FIG. 1B). The degradation of photosystem I subunits (PsaB), photosystem II subunits (D1, PsbO1, and Lhcb2) and stroma protein GS2 were clear in wild-type plants after 10 days of salt treatment. In amiR-AtCV plants, the abundance of the above-mentioned chloroplast proteins only decreased slightly after 16 days of salt treatments. These results demonstrated that silencing AtCV inhibited the salt stress-induced degradation of chloroplast proteins. In addition, the chloroplast degradation caused by MV-induced oxidative stress was also delayed in amiR-AtCV lines. Moreover, their survival rates increased significantly after 14-day drought treatment (FIG. 2). These results indicated that silencing AtCV increased chloroplast stability and prevented abiotic-stress-induced senescence.

The C-Terminal Domain of AtCV is Important for Chloroplast Destabilization and the Formation of CCVs.

A search of sequences similar to AtCV in the public genome databases showed the presence of AtCV homologs in all plant species sequenced so far. These genes contain a unique highly conserved domain at the C-terminus of the encoded proteins. Without the conserved C terminus domain, AtCVΔC-GFP still localized at the chloroplasts but hardly produced vesicles. Moreover, the DEX-induced expression of AtCVΔC-GFP produced some leaf senescence and partial chloroplast degradation. Nonetheless, the destabilizing functions of AtCVΔCGFP were substantially impaired, as compared with the plants expressing the full-length AtCV-GFP, indicating a key role of the conserved C-terminus domain of AtCV in chloroplast destabilization and the formation of CCVs.

AtCV Interacts with Photosystem II Subunit PsbO In Vivo

To elucidate mechanism(s) by which AtCV disrupts chloroplasts, we identified AtCV potential interacting proteins using co-immunoprecipitation (Co-IP) and subsequent identification of interactors by LC-MS/MS (Smaczniak et al. 2012, Nat Protoc 7: 2144-2158). Antibodies raised against HA were conjugated to magnetic beads, and the beads were used to immunoprecipitate AtCV-HA and its interacting proteins from total protein extracts obtained from DEX-treated transgenic plants expressing DEX:AtCV-HA (DEX-3 line). Protein extracts from wild type Col-0 plants were used as a control to detect proteins that bind nonspecifically to the anti-HA beads. Most of immunoprecipitated proteins were chloroplast proteins including Photosystem II (PSII) complex subunits, NAD(P)H Dehydrogenase subunits, thylakoid membrane-bound proteases, and a few stromal proteins. The similarity between the peptide abundances of PSII subunits PsbO1, PsbO2 and the bait protein AtCV and their localization and functions would indicate the interaction between AtCV and PsbO proteins. In order to confirm this interaction, we used bimolecular fluorescence complementation (BiFC). The transient expression of both fusion genes AtCV-SCFPC and PsbO1-VenusN in cotyledons of wild type seedlings resulted in BiFC fluorescence that was seen not only in the chloroplasts but also in the CCVs, whereas the coexpression of AtCV-SCFPC and SGR1-VenusN failed to produce green fluorescence signals in three independent tests. These results indicated a direct interaction between AtCV and PsbO1 in vivo. Interestingly, the co-expression of the N-terminus fusion SCFPC-PsbO1 and VenusN-AtCV also induced fluorescence, which was not associated with chloroplasts, suggesting that the N-terminal fusion did not affect the interaction between AtCV and PsbO1, but misled proteins to other location (perhaps cytosol) rather than chloroplast because of the disruption of the N-terminus chloroplast transit signal peptide of AtCV and PsbO1.

We also constructed another mutation AtCVΔC by deleting the AtCV C-terminus conserved domain. No fluorescence was detected between AtCVΔC-SCFPC and PsbO1-VenusN. These results indicated that the conserved C-terminus domain was required for the interaction between AtCV and PsbO1. This notion was further confirmed by the Co-IP results showing that the full length AtCV, but not AtCVΔC, was immunopreciptated by using anti-PsbO1 antibody. In addition, we transiently co-expressed AtCV-YFP together with PsbO1-CFP in wild type seedlings. In cells without AtCV-YFP, the PsbO1-CFP was distributed uniformly in chloroplasts. However, AtCV-YFP expression altered the localization of PsbO1 and caused the concentration of PsbO1-CFP in the AtCV-containing vesicles. Collectively, these finding suggested that AtCV could disrupt the localization of PsbO1 in chloroplasts, possibly through direct protein-protein interaction.

In addition to the stroma-targeted DsRed and PSII subunit PsbO1, we also observed two more thylakoid proteins "wrapped" in CCVs. The gene encoding the thylakoid lumen protein AtCYP20-2, an immunophilin associated with the PSI/NDH supercomplex (Sirpio et al. 2009, Febs Letters 583: 2355-2358), was cloned and fused with CFP. The AtCYP20-CFP construct was co-expressed transiently with AtCV-GFP in cotyledons and confocal microscopy observations clearly showed their co-localization. Also, the gene encoding the thylakoid membrane-bound FtsH protease was fused to CFP and the AtFtsH1-CFP was co-expressed with AtCV-GFP. Our results showed that AtFtsH1-CFP and AtCV-GFP overlapped both in chloroplast and in CCVs released from the chloroplast. However, the plastoglobule marker protein plastoglobulin 34, PGL34-YFP (Vidi et al. 2007, BMC Biotechnol 7), did not overlap with AtCV-RFP, suggesting that the plastoglobule turnover was independent of the AtCV-induced degradation pathway.

Discussion

AtCV Regulates Stress-Induced Chloroplast Degradation Through a Pathway Independent of Autophagy and SAVs Plants use different strategies to cope with environmental stress. The "escape" strategy involves the fast degradation of source tissues and the accelerated development of sinks, contributing to a faster life cycle and the production of seeds for the next generation (Levitt 1972, Annu Rev Plant Biol 58: 115-136). Chloroplasts contain large amounts of proteins, and the fast and massive chloroplast degradation during stress is a key process that provides nutrients for relocation to developing organs (Makino and Osmond 1991, Plant Physiol 96: 355-362). In this study, we identified a gene AtCV encoding a protein that mediates the turnover of chloroplast proteins. Our results showed that silencing AtCV delayed the stress-induced chloroplast degradation and leaf senescence while AtCV overexpression caused chloroplast degradation and premature leaf senescence.

Previous studies revealed two extra-plastidic proteolytic processes, autophagy (Ishida et al. 2008, Plant Physiol 148: 142-155; Wada et al. 2009, Plant Physiol 149: 885-893) and SAVs (Otegui et al. 2005; Martinez et al. 2008, Plant Journal 56: 196-206; Carrion et al. 2013), that are involved in the degradation of chloroplasts. However, little is known about the factors regulating intra-plastidic chloroplast degradation. Our results revealed a novel proteolytic pathway, which is independent of autophagy and SAVs, and is mediated by the formation of AtCV-containing vesicles. AtCV expression is elicited by tissue senescence or stress-induced senescence. After targeting the chloroplast, AtCV is able to induce the formation of vesicles in chloroplasts (CCVs) through a mechanism that is unclear so far. The CCVs are eventually released from the chloroplast to the cytosol carrying away some "cargo" proteins from the chloroplast. In addition to stromal protein, CCVs were shown to contain the thylakoid membrane protein FtsH1, lumenal proteins PsbO1 and AtCYP20-2, and the inner envelope membrane protein Tic20-II.

Based on the immunolabeling results, AtCV proteins are mostly associated with thylakoid membrane and envelope membrane before the formation of CCVs, likely via its putative transmembrane domain. Confocal microscopy observations also demonstrated the co-localization of AtCV and the inner envelope membrane protein Tic20-II. Although the exact mechanism of vesicle formation remains elusive, these results, together with our observations showing that the AtCV-induced vesicle formation were coupled with the unstacking and swelling of the thylakoid membranes and the disassembling of the chloroplast structure, support the notion that the CCVs can form directly from the chloroplast membranes disrupted by AtCV.

Autophagy induces the formation of Rubisco-containing bodies (RCBs) by engulfing the stromules protruding from chloroplasts and the chloroplast functions are still maintained (Ishida et al. 2008). As compared with autophagy-dependent degradation, AtCVmediated degradation appears to be more destructive. AtCV-mediated chloroplast damage leads to leaf senescence, as observed during DEX-induced AtCV over-expression.

Interestingly, silencing AtCV did not delay the natural leaf senescence. A possible explanation of this phenomena is that other pathways, such as autophagy (Ishida et al. 2008, Plant Physiol 148: 142-155; Wada et al. 2009, Plant Physiol 149: 885-893), SAVs (Otegui et al. 2005, Plant Journal 41: 831-844; Martinez et al. 2008 Plant Journal 56: 196-206; Carrion et al. 2013, J Exp Bot 64: 4967-4980) or SGR-mediated chlorophyll degradation (Park et al. 2007, Plant Cell 19: 1649-1664; Ren et al. 2007, Plant Physiology 144: 1429-1441; Hortensteiner 2009, Trends Plant Sci 14: 155-162; Sakuraba et al. 2012), might be enhanced in AtCV-silenced plants for destabilizing chloroplasts and accelerating senescence. The possible interactions between the processes of autophagy, SAVs and AtCV-dependent degradation are unknown and require further investigation.

AtCV Mediates Chloroplast Destabilization and Vesiculation

Co-immunoprecipitation and subsequent analysis by LC-MS/MS revealed several proteins having potential interaction with AtCV. We confirmed that AtCV targets PSII subunit PsbO1 in vivo by BiFC assays. Another PsbO gene product, PsbO2, that shares 91% similarity with PsbO1 in amino acid sequence, was also immunoprecipitated by AtCV, suggesting the AtCV-PsbO2 interaction.

In spite of its role in stabilizing Manganese, PsbO is thought to play a chaperone-like role in PSII assembly (Yamamoto 2001, Plant and Cell Physiology 42: 121-128, Plant and Cell Physiology 42: 121-128; Yamamoto et al. 2008, Photosynth Res 98: 589-608). Although PsbO1 and PsbO2 functions are not completely redundant (Lundin et al. 2007, Plant Journal 49: 528-539), RNAi silencing of both genes (Yi et al. 2005, Journal of Biological Chemistry 280: 16170-16174) lead to a decreased stability of PSII and the loss of some photosynthetic proteins, including CP47, CP43, D1, and even the PSI core protein PsaB, while the light-harvesting complex II (LHC II) was stable in PsbO RNAi lines (Yi et al. 2005, Journal of Biological Chemistry 280: 16170-16174). In AtCV overexpressing lines, D1 and PsaB were degraded while the stability of Lhcb2 was less affected as compared with other PSII proteins. Furthermore, CP43 and D1 were also immunoprecipitated by AtCV. Altogether, these results strongly suggested the functional interaction between AtCV and PsbO. AtCV targeted PsbO directly and might alter the structure of PSII complex, removing PsbO, affecting PSII stability, and making core proteins (such as D1) very susceptible to thylakoid proteases. The proteases Deg (Kapri-Pardes et al. 2007, Plant Cell 19:1039-1047) and FstH (Lindahl et al. 2000, Plant Cell 12: 419-431; Zaltsman et al. 2005, Plant Cell 17: 2782-2790; Shen et al. 2007, Plant J 52: 309-321; Adam et al. 2011, Plant Cell 23: 3745-3760) have been identified to be responsible for the turnover of D1 protein. Interestingly, both DegP1 and FstH1 appeared to interact with AtCV and FstH1-CFP colocalized with AtCV-GFP in vivo. Taken together, these results suggest a mechanism by which AtCV might facilitate the approach of proteases to D1 protein after removing PsbO. AtCV-dependent removal of PsbO promotes PSII turnover and destabilizes chloroplasts. In addition, previous in-vitro studies revealed that the aggregation of D1 and other subunits including CP43 occurred in the absence of PsbO (Henmi et al. 2003, Plant and
Cell Physiology 44: 451-456; Yamamoto et al. 2008, Photosynth Res 98: 589-608). Thus, AtCV-induced elimination of PsbO could cause the aggregation between D1 and other PSII core proteins, and this aggregation could signal for vesicle formation. Supporting this notion, it has been shown recently that the over-expression of triple gene block3 (TGB3) of Alternanthera mosaic virus in *Nicotinana benthamiana* caused chloroplast vesiculation and veinal necrosis by interacting with the host PsbO (Jang et al. 2013, Front Plant Sci 4). AtCV interacts with PsbO1 by a Cterminus domain which is highly conserved in the plant kingdom. The conserved domain appeared to be important for vesicle formation and chloroplast degradation. However, the deletion of the conserved domain did not completely eliminate chloroplast function. Several chloroplast proteins, in addition to PsbO, were also immunoprecipitated by AtCV, suggesting that PsbO1 may not be the only protein targeted by AtCV during the process of chloroplast degradation.

Increase Stress Tolerance Through Stabilizing the Chloroplast

Abiotic stress limits plant growth and productivity by disrupting photosynthesis and inducing senescence. Emerging evidence suggested that chloroplast stability plays a significant role in the tolerance of plants to abiotic stress. Senescence and stress-induced synthesis of cytokinin synthesis delayed the degradation of photosynthetic complexes in transgenic plants expressing PSARK:IPT plants that displayed enhanced drought tolerance (Rivero et al. 2010, Plant and Cell Physiology 51: 1929-1941). In addition, a wheat stay-green mutant (tasg1) displayed a delayed chlorophyll turnover and improved tolerance to drought because of the enhanced stability of thylakoid membranes (Tian et al. 2013, J Exp Bot 64:1509-1520). The stable chloroplasts could also contribute to maintain photorespiration which has been shown to increase the tolerance to abiotic stress by protecting the photosynthetic apparatus from oxidative damage and optimizing photosynthesis (Rivero et al. 2009, Plant Physiology 150: 1530-1540; Voss et al. 2013, Plant Biology 15:713-722). Here, we showed that silencing AtCV increased the chloroplast stability and prevented premature senescence under salt, oxidative and drought stress (FIG. 1). Our results would indicate that AtCV acts as a scaffold targeting PSII proteins directly. Thus silencing AtCV may protect PSII functions, increasing plant tolerance to abiotic stress. Moreover, AtCV-silenced plants displayed increased glutamine synthase 2 stability. GS2 is a major enzyme for nitrogen assimilation, and GS2 overexpression lead to increased salt stress tolerance in rice (Hoshida et al. 2000, Plant Mol Biol 43: 103-111).

In conclusion, our results provide evidence supporting a novel pathway for the degradation of thylakoid and stromal proteins that is independent of autophagy (Ishida, 2008 Autophagy 4: 961-962) and SAVs (Otegui et al. 2005, Plant Journal 41: 831-844; Martinez et al. 2008, Plant Journal 56: 196-206; Carrion et al. 2013). While authophagy is responsible for general cellular degradation, AtCV appears to be unique and specific for chloroplast degradation. From a biotechnological perspective, silencing of AtCV offers a suitable strategy for the generation of transgenic crops with increased tolerance to abiotic stress.

Example 2

This example shows that rice lines expressing amiRNAs are resistant to drought stress. Transgenic rice plants were prepared according to standard techniques using the amiRNAs described above.

Figure 3:
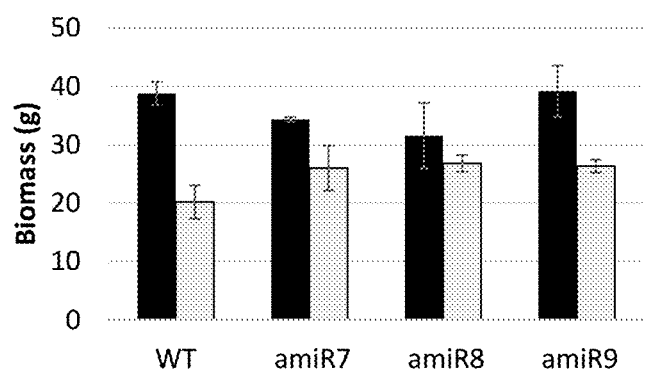
FIG. 3 shows the results of drought stress experiments carried out using transgenic rice plants expressing amiRNAs of the invention.
Figure 3:
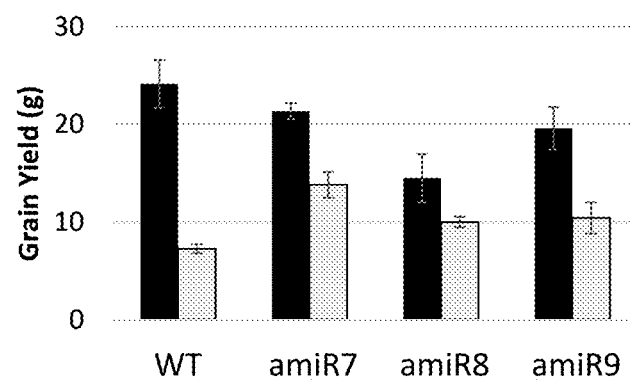

Wild type and 3 transgenic rice lines expressing amiRNAs were grown in the greenhouse under well watered conditions (black bars in FIG. 3) and subjected to water deficit stress (water withheld for 6-8 days, gray bars in FIG. 3). Plants were re-watered and seeds were collected. Results in FIG. 3 show that although the transgenic plants displayed some yield penalty at well-watered conditions, they yielded significantly more seeds after the stress event.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING
>AT2G25625 (*Arabidopsis thaliana*)

SEQ ID NO: 1

ATGGCAGGGAGAATAAGCTGCTGTCTAAATCTTCCTCCCCTAGATTCAAATTCTG

CACAATCATTAGCTTCACTGCTCAAGACAACGTCAAAGATCTCTTGTAGGAGAAC

AGAAAATGAGACAGAGCCACGGAAAAACAAGTGTTCTTTTGTCTTGGGGGTGGC

GGCAACTGTCGTAATCGGCGGGATTCAGATCAATGATGTTGCATCAGTGGAAGCT

GCGGTTGTGAAATCGCCGGTAGAAGAGATGGCTGCGGGTGTGGTGCCGCCGCGG

AGGTGGAGTGACAAGAGGACGTGTCCGCTTGGCTTGAGAACTCGCTAGAGACC

ATCGTACCGGAGAATCTTCCTCGTCCGTCTGCTCATCGACGTTTGGAGTTAGCCG

GATTAGCTAAGGGTGATGCACCGCCGGTCGGTGTGGTGATGACACGTGTCAACA

GGGGTGGTTGTTTCTCCGTGTAA

SEQ ID NO: 2

MAGRISCCLNLPPLDSNSAQSLASLLKTTSKISCRRTENETEPRKNKCSFVLGVAATV

VIGGIQINDVASVEAAVVKSPVEEMAAGVVPPRRWSDKRTCPPWLENSLETIVPENL

PRPSAHRRLELAGLAKGDAPPVGVVMTRVNRGGCFSV

>BD2G15690 (*Brachypodium distachyon*)

SEQ ID NO: 3

ATGCCGGTCTCCTCCGCCATCAGCTGCTGCCAGCAGCTCAGACCTCCGGGTCCAC

CTCCGGCGCCGAGAGAAGAAGGCAGCAGCAGCAGTAGTCGTATCCCGCTGTCGC

GGCGCAGGGCGTGCTTTCTCGCGGCGGCGGCGGCGTGCGTGGTGGCCGTGGCGG

CGGGAGGGGCCGGAGAAGCAGCGGCGATGGCGCGGGGCGCGCCGCACGAGCAC

GAGGCGGCGGCGGCGGTGCGCGTGCAGGCTGGGGCGGCGGCGAGGTGGAGCGA

GCGCAGGCAGTGCCCGCCGTGGCGGGCGAATTCGCTGGAGAACGTAGTGCCGGA

GAACCTGCCGCGCCCGTCGGCGCGGCGGAGGTACAACGGCGTCGGGGAGAGGG

ATCCCGCGCCGGCGCCAGCCGCGTCGCCTGAGGCCGTGCTCCCGTTCCTGGCGCT

GCGCTCCGGCGGCATGGGCTGCTTCTCTCTCTAA

SEQ ID NO: 4

MPVSSAISCCQQLRPPGPPPAPREEGSSSSSRIPLSRRRACFLAAAAACVVAVAAGGA

GEAAAMARGAPHEHEAAAAVRVQAGAAARWSERRQCPPWRANSLENVVPENLPR

PSARRRYNGVGERDPAPAPAASPEAVLPFLALRSGGMGCFSL

>CP00603G00010 (*Carica papaya*)

SEQ ID NO: 5

ATGGATATGGAGGATAGATTACAGAAGAAATGTGGAGATTTGAGCCTGATCTAC

TCCGGAAGACATGAGAGAGGTTTTTGGGCGATTGACACGAGGATTCCTGGTTTCC

GGCGAATGCTCAGGAACAATGTGAAGAGGAGTCGTCTGGTTAAACGAAACGGTA

GAGAGGGAGAGAGTGAAGATGATGGCGATGAGAGTAAGTTGCTGCCTAAACCTT

CCTCCTCGAGAAAAACCTTCACTCCATCTCCCTCCTCCTGCCAACACGTTTTCTCA

ATTACCTTCAAGGAAAAAGGAAGAATGTTGGAGGAAGAAGAGTGCGGTGGCGAT

GGCGTGCTTGGTAATTGGATTGATACAGGTGGCAAATGGAGCGAAAAGAGAATG

TGTCCGCCATGGCATGCTAACTCCCTTGAGACCGTCGTGCCGGAGAATCTCCCTC

GGCCATCTGCTCGTCGGAGATGGCAGCTTGTTGCTTTCACCCCCAACCTTCGTCA

GCCCCCACCCACATGTTTCTCTTTGTGA

SEQ ID NO: 6
MDMEDRLQKKCGDLSLIYSGRHERGFWAIDTRIPGFRRMLRNNVKRSRLVKRNGRE

GESEDDGDESKLLPKPSSSRKTFTPSPSSCQHVFSITFKEKGRMLEEEECGGDGVLGN

WIDTGGKWSEKRMCPPWHANSLETVVPENLPRPSARRRWQLVAFTPNLRQPPPTCF

SL

>FV2G40830 (Fragaria vesca)
SEQ ID NO: 7
ATGGCCATGACAAGCTTCAGCTGCAGCCTTAACCAGCTGCCGCCTCCAGCTCAAA

GCTTAGGCCCTTCTTCCCCTTCAAAGACGAATCAAGTACAACTTGCATGGAACAA

AAGCGAGGGAGGATCATGGAGTAGCAGATGTGTTGTGGGCATGGCTTGTGTTAT

GGTTGGGTTGGAGATGGGTGGTTTGGTGAGTGGCCAAAGCCATGAAGCTATTGCT

AAAGGTATGCCGCCGTTGGTGATGGAGTCAAGTGAGAAAGTTGCAAAGTGGAGT

GACAAGAGAATGTGCCCAAAGTGGAGAGCCAATGAGCTGGAGACCATTGTGCCG

GAGAATCTTCCGAGGCCGTCGGCTCACCGGAGATGGGAAATCGTCGGGTTTAAT

ACTAGGGATGCTCCGGCGGTTAAGACGGTAGCTAGGAGGAGTAGCGGTGGTTGC

TTTTCTATGTAA

SEQ ID NO: 8
MAMTSFSCSLNQLPPPAQSLGPSSPSKTNQVQLAWNKSEGGSWSSRCVVGMACVM

VGLEMGGLVSGQSHEAIAKGMPPLVMESSEKVAKWSDKRMCPKWRANELETIVPE

NLPRPSAHRRWEIVGFNTRDAPAVKTVARRSSGGCFSM

>GM04G07440 (Glycine max-1)
SEQ ID NO: 9
ATGAGGACCACTTGCTTACTAAGCCTTCCCCCTCTTACTTCAAACCAACCCTCCA

ACGCTTCTTTCAACCCCGCAAAGCCACCTCAACTTTCATCGCAATGCGTTATGAT

GGGAGTGGCATCCATAATTGGACTAGAAATGTGCAATTTAGTGGCACTGGCCCA

CGAAGCAATTGAAATCACAACTATGCCAATTGGTAACCAAGTAAAAGAACGTG

CTCACCTTGGCAAGGCAACTCGCTCGAAACCATCATGCCGGAGAACCTTCCCCGG

CCGTCGGCACGGCGGCGATACGAGGCTGTTCGTTCCTCCACCAAGACTGTGCCAC

CGTCCTCAGCCCCGATCATAGTCCAAAGCAACAAGGGCAGCTGCTTCTCCATGTG

A

SEQ ID NO: 10
MRTTCLLSLPPLTSNQPSNASFNPAKPPQLSSQCVMMGVASIIGLEMCNLVALAHEAI

EITTMPIGNQVKRTCSPWQGNSLETIMPENLPRPSARRRYEAVRSSTKTVPPSSAPIIV

QSNKGSCFSM

>GM06G07560 (Glycine max-2)
SEQ ID NO: 11
ATGAGGACCAGTTGCTTCCTAAGCCTTCCCCCTTTTACTTCAAACCAACCTTCCAT

TCCCCCAAAACATCCTCAACTTTCATCGGTGAAGAACGAAGCATGTTGGAAGAG

GCAATGCGTTGTGATGGGAGTGGCATCCATTATTGGACTAGAAATGTGCAATTCA

GTGGCAATGGCCCACGAAGCAATTGAAATCAAGACCATGCCATTTAGTAACCAA

GTAGTATCAAATAGCAATTCTTACGGTGGCGCCAAATGGAGCGAGAAAAGAATG

TGCCCACCTTGGCAAGGCAATTCGCTCGAAACGATCGTGCCGGAGAATCTTCCCC

GGCCGTCGGCACGGCGGAGATACGAGGCTGTTCGTTCCTCCTCCAAGACTGCGCC

GCCGCTCTCCGCCCCGATCATAGTCCAAAGCAACAAGGGCAGTTGCTTCTCCATG

TGA

-continued

```
                                                    SEQ ID NO: 12
MRTSCFLSLPPFTSNQPSIPPKHPQLSSVKNEACWKRQCVVMGVASIIGLEMCNSVA

MAHEAIEIKTMPFSNQVVSNSNSYGGAKWSEKRMCPPWQGNSLETIVPENLPRPSAR

RRYEAVRSSSKTAPPLSAPIIVQSNKGSCFSM

>LJ0G026030 (Lotus japonicus)
                                                    SEQ ID NO: 13
GCCAAATGGAGCCAGAAAAGGGCGTGTCCTCCTTGGCGAGGTAACGCTTTGGAA

ACCATCGTGCCGGAGAATCTTCCGCGGCCAGCGGCGCGGCGGAGATACGAGGCT

GTTCGGTCAACCTCCAAGACGGCGCCGCCGCTCTCTGAAGCCTTCAAAATTAAAT

CCAACAGTTATAGTTGCTTCTCCATG

SEQ ID NO: 14
AKWSQKRACPPWRGNALETIVPENLPRPAARRRYEAVRSTSKTAPPLSEAFKIKSNS

YSCFSM

>MD00G178660 (Malus domestica-1)
                                                    SEQ ID NO: 15
ATGGCTTGTTTTAGAGGGTCACCATTGAGGTCTTTGTCATCTCTTTTAACCTTATG

CAACCAAACCCACCTTCCTCTTTTGATATATACGATCCCTCTCCTTCTGTCATTGC

TTAAATTCAGAGAGAACAGAGAGAGAGAGAGAGAGAAAGGGATGACTGTTACA

AACTTCAATTGCTGCCTCAATCCGCCACCTTCAAATCAAAACCATGGTTCAAGCC

CTTCTTTGCCCTTAAAGAAAAACCAAGCACTTGCATGGAACAAATATGCTCATGG

ATCATGGACTAATCGATGCGTTTTAGGTATGAGTTGCGCAATTGGATTGGAAATG

GGAACCCTAGTAAGCAACCAAAACTATGAGGCCATTGCTAATGCTATGCCTTCGC

CGTTGGAAATAGAAACATATAGTGATCAGAGGGTTGAAAAATGGAGTGACAAAA

GAATATGCCCACAATGGAGCCCTAATTCACAAGAGACCATTGTGCCTGAAAATCT

CCCAAGATCATCTGCTCAAAGGAGATGGGAAACAGTTGGTTTTTCTAACGAGGAT

GCTCCGGCGGTTCAAATGGTAGTTAGAAAAGGTGGCAACTGCTTTGCTATGTAG

SEQ ID NO: 16
MACFRGSPLRSLSSLLTLCNQTHLPLLIYTIPLLLSLLKFRENREREREKGMTVTNFNC

CLNPPPSNQNHGSSPSLPLKKNQALAWNKYAHGSWTNRCVLGMSCAIGLEMGTLVS

NQNYEAIANAMPSPLEIETYSDQRVEKWSDKRICPQWSPNSQETIVPENLPRSSAQRR

WETVGFSNEDAPAVQMVVRKGGNCFAM

>MD00G406410 (Malus domestica-2)
                                                    SEQ ID NO: 17
ATGACTGTTACAAACTTCAATTGCTGCCTCAATCCGCCACCTTCAAATCAAAACC

ATGGTTCAAGCCCTTCTTTGCCCTTAAAGCAAAACCAAGCACTTGCATGGAACAA

ATATGCTCATGGATCATGGACTAATCGATGCGTTTTAGGTATGAGTTGCATCGCA

ATTGGATATGAAATGGGAACCCTAGTAAGCAACCAAAACTATGAGGCCATTGCT

AATGCTATGCCTTCGCCGTTGGAAATAGAAACATCAAGTGATCAGAGGGTTGCA

AAATGGAGTGACAAAAGAATGTGCCCACAATGGAGCCCTAATTCGCTAGAGACC

ATTGTGCCTGAAAATCTTCCAAGACCATCTGCTCAAATGAGATGGGAAACCGTTG

GTTTTTCTGACAAGGATGCTCCGGTGGTTCAAATGGTAGTTAGAAAAGGTGGCAG

CTGCTTTGCTATGTAG
```

SEQ ID NO: 18
MTVTNFNCCLNPPPSNQNHGSSPSLPLKQNQALAWNKYAHGSWTNRCVLGMSCIAI
GYEMGTLVSNQNYEAIANAMPSPLEIETSSDQRVAKWSDKRMCPQWSPNSLETIVPE
NLPRPSAQMRWETVGFSDKDAPVVQMVVRKGGSCFAM

>MD14G005720 (Malus domestica-3)

SEQ ID NO: 19
ATGGCTTGTTTTAGAGGGTCACCATTGAGGTCTTTGTCATCTCTTTTAACCTTATG
CAACCAAACCCACCTTCCTCTTTTGATATATACGATCCCTCTCCTTCTGTCATTGC
TTAAATTCAGAGAGAACAGAGAGAGAGAGAGAGAGAAAGGGATGACTGTTACA
AACTTCAATTGCTGCCTCAATCCGCCACCTTCAAATCAAAACCATGGTTCAAGCC
CTTCTTTGCCCTTAAAGAAAAACCAAGCACTTGCATGGAACAAATATGCTCATGG
ATCATGGACTAATCGATGCGTTTTAGGTATGAGTTGCGCAATTGGATTGGAAATG
GGAACCCTAGTAAGCAACCAAAACTATGAGGCCATTGCTAATGCTATGCCTTCGC
CGTTGGAAATAGAAACATATAGTGATCAGAGGGTTGAAAAATGGAGTGACAAAA
GAATATGCCCACAATGGAGCCCTAATTCACAAGAGACCATTGTGCCTGAAAATCT
CCCAAGATCATCTGCTCAAAGGAGATGGGAAACAGTTGGTTTTTCTAACGAGGAT
GCTCCGGCGGTTCAAATGGTAGTTAGAAAAGGTGGCAACTGCTTTGCTATGTAG

SEQ ID NO: 20
MTVTNFNCCLNPPPSNQSHGSSPSLPSKQNQVPAWNKNDHGSWAKRCVVGMSCIMI
GFEMGSVVSNQTHEAIAKVMPLPLEIATSSDQRVAKWSEKRMCPQWSXNSLETIVPE
NLPRPSAQRRWEAVGFSKDAPAVQMVVRKGGNCFAM

>ME00847G01190 (Manihot esculenta-1)

SEQ ID NO: 21
AAATTCAAAGAAAGGGTCAAGGCGAATGCGATTGCCTTGGCCGGGTTGAAGAAC
GACAAGTGGAGAAGCCAATGTTTACTGGGCATGGCATGCATCATAATTGGGCTT
GAGATGGATTTGGCCAGCCATGAAAATCTTGCGGCGGCCGAAGATTTGCAATTTT
CACTTGGGGAATCTAAGGAGAAAACCAAGAGATACAGATGGAGTGACAAAAGA
ATGTGTCCTCCATGGCGTCTTAATGCACTAGAGACCATTGTGCCTGAGAACCTAC
CAAGGCCATCAGCTCGACGGAGATGGGAGGCGATTGATTATTCAAAGATTGTTC
CAGCTCCGGCTCCGGCAATTAAAGTGATAATCAGAAGCAGCAAGAATTGCTTTA
CTATGTAA

SEQ ID NO: 22
KFKERVKANAIALAGLKNDKWRSQCLLGMACIIGLEMDLASHENLAAAEDLQFSL
GESKEKTKRYRWSDKRMCPPWRLNALETIVPENLPRPSARRRWEAIDYSKIVPAPAP
AIKVIIRSSKNCFTM

>ME04796G00360 (Manihot esculenta-2)

SEQ ID NO: 23
ATGGCCATTGCACCCAGTTGCTGCCTCAATCTCCGCCCTCCAACTCCACCCTCACC
TCCTCCCAATGCAAGGGCTACCCAAGCTGCATGGTTCAAGAACGGCAGCTGGAG
AAGCCAGTGTGTAGTGGGCATGGCCTGCATCATAATTGGAGTTGAAATGGATTTG
GCGAGTCAAGCAAATGTTGCCACAGCCAAAGACTTGCAATATTTACTTGTAGAGT
CGAAGGAGAACACCAAAGGTGACAGATGGAGTGACAGAAGAATTTGTCCTCCTT
GGCATCTTAATTCGCTAGAGACCATTGTGCCGGAGAACCTTCCAAGGCCGTCGGC
TCGTCGGAGATGGGAAGAGGTTGGTAATGTAAAGAATGTTCCGGCTCCGGCGAT
TAAAGTGATAGTTAAAAGCCGTAGCAGCAGCAACAATTGCTTTACCATGTAA

```
                                                        SEQ ID NO: 24
MAIAPSCCLNLRPPTPPSPPPNARATQAAWFKNGSWRSQCVVGMACIIIGVEMDLAS

QANVATAKDLQYLLVESKENTKGDRWSDRRICPPWHLNSLETIVPENLPRPSARRR

WEEVGNVKNVPAPAIKVIVKSRSSSNNCFTM
```

>MT3G107890 (*Medicago truncatula*)

```
                                                        SEQ ID NO: 25
ATGACATCAACCAGTTGCTGCCTCCGTCTTTACCCTACAACTTCAAACGCTTCTCT

CATCCCTAAAAACTCACCTCAACTTTCCTCGGAGATCAAAAACAGTGGATGCTGG

AGAAGGCGGTGTGTTGTGATAGGAGTGGCTTCGTGCTTCTCTATAATTGGACTAC

AATTCAACAATTCAGTGTCATTGGAACATGAAGCTGTGGCTAAGGAGAATACCA

TGTTGGTGGCCATGTCAAATTCAATAGATGATGATGATGAGCATGTGTTTTTGGT

TGGTGGTGCGGCCAAATGGAGCCAGAAAAGGATGTGCCCCTCTTGGCAAGGAAA

CAATCCCCTCGAAACCATCGTGCCAGAGAATCTTCCACGGCCAGCAGCACGTCG

GAGATATGAGACTGTTCGCTCCACCTCTAAGATTGCTCCACCACTCTCAATGTCC

GTCAAACTTAAAACCAATAGGGACAGTTGTTTCTCCATGTGA

SEQ ID NO: 26
MTSTSCCLRLYPTTSNASLIPKNSPQLSSEIKNSGCWRRRCVVIGVASCFSIIGLQFNNS

VSLEHEAVAKENTMLVAMSNSIDDDDEHVFLVGGAAKWSQKRMCPSWQGNNPLET

IVPENLPRPAARRRYETVRSTSKIAPPLSMSVKLKTNRDSCFSM
```

>FQ394381 (*Vitis vinifera*)

```
                                                        SEQ ID NO: 27
ATGGCCTTCTCTGCTGGTTGCTGCCTCAATCTCTCGCCTCCACCATCTGGGTCCAG

CCCACGATCTTCTCGAAGCTCAACTAAAACTGATCAAGTTTCATGGCCAAGAAAA

GAAAATTCATTGAAGAGCAAATGTCTCGTGGGGTTGACATGCATGATAATAAGC

TTAGAAATGTCCAATTTAATGAGTGGTGAAGGGCTGGCCATTGCCCAAGATTTGC

AATTAATTGGTGAAAGAAAAGAGGTAACGAGGTGGAGCGACAAGAGAATGTGC

CCGCCCTGGCAGCTCAACTCATTGGAGACAATTGTGCCGGAGAACCTTCCCCGGC

CGTCGACTCGCCGGAGATGGGAGTCAGTTGGTCATTCCACAACTGCCCCGGCAGT

AAAAATTCTATTTAGAGCTCACACCAAGTCAGATTGTTTTTCCATGTGA

SEQ ID NO: 28
MAFSAGCCLNLSPPPSGSSPRSSRSSTKTDQVSWPRKENSLKSKCLVGLTCMIISLEM

SNLMSGEGLAIAQDLQLIGERKEVTRWSDKRMCPPWQLNSLETIVPENLPRPSTRRR

WESVGHSTTAPAVKILFRAHTKSDCFSM
```

>OS05G49940 (*Oryza sativa*)

```
                                                        SEQ ID NO: 29
ATGGTGGTCTCCTGCCAGCTCAAGCCTGCGCCGGCTCCGGCCGCCGCCAGCAGAG

GCGGCGGCGCGCCTCACCTCCAGCAGCTGCGCCGGGCGTGCGTCGCGGCGGCGG

CGGCGTGCGCGGTGCTCGGGACGGCGGGCGGCCCCGGCGAAGGCGCCGTGATGG

CGCGTGCGCCGGAGGCGACGGCGGCGGCGGCGGGGCCGGCGCGGTGGAGC

GACCGCCGGCAGTGCCCGCCGTGGCGCGCCAACTCGCTGGAGAACATCGTGCCG

GAGAACCTGCCGCGGCCGTCGGCTCGCCGGAGGTTCAACAGCATCACGGCGGCG

GCGGCGGCGGAGAGCGCGCCGCCCCCCGCGTCGGCGTCGCCCGACGCCGTGCTC

CCGTTCTTGGCGCCGCGCTCCGGCATGGGCTGCTTCTCCCTCTAA
```

-continued

SEQ ID NO: 30
MVVSCQLKPAPAPAAASRGGGAPHLQQLRRACVAAAAACAVLGTAGGPGEGAVM

ARAPEATAAAAAGPARWSDRRQCPPWRANSLENIVPENLPRPSARRRFNSITAAAAA

ESAPPPASASPDAVLPFLAPRSGMGCFSL

>PT06G24730 (*Populus trichocarpa*)
SEQ ID NO: 31
ATGGCCATCAGAACTACTTGTCGCCTCAATCTCTCCCCTCCAGGCTCTGGCTCAA

CCCTCCCTTCTTCCTCTACAAAGAACTCCCAGGTTGCCTGGTTCAAGAATGAAAA

GTGGAGGAATCGATGTGTACTGGGCGCGGCGTGCATGATAATTGGACTTGAAAT

GGGAGGTGGTTTAGTGGGTGGTGAAGATCTTGCCATGGCTAGGGAGATGCAGGT

GGCTGTGGAATCAAAAGAAAACTTGAATGGGCCAAGGTGGAGTGACAAGAGAA

TGTGCCCTCCATGGAGTCGGAATTCGCTAGAGACTATTGTGCCGGAGAACCTTCC

AAGGCCATCGGCTCATAGGAGGTGGGAAGAAGTTCGCTTTTCCAAGAACAATGC

TCCGGCCGTCAAAGTGATTGTGATCAAAAGAAGCAACGGTTGCTTCTCCATGTAA

SEQ ID NO: 32
MAIRTTCRLNLSPPGSGSTLPSSSTKNSQVAWFKNEKWRNRCVLGAACMIIGLEMGG

GLVGGEDLAMAREMQVAVESKENLNGPRWSDKRMCPPWSRNSLETIVPENLPRPSA

HRRWEEVRFSKNNAPAVKVIVIKRSNGCFSM

>RC29912G02840 (*Ricinus communis*)
SEQ ID NO: 33
ATGGCCATTACAACTAGTTGCTGCCTCAATATGAATATCCCTCCTCCAACTAGTG

CTTCAAGTCTACCTTCTTCTTCTTCTACTACAAAGCCCACTGCTCAAGCCTCTTGG

TTCAAGAATGAGAAGTGGAGAAGCCAATGTGTACTAGGCATGGCCTGCATGATA

ATTGGACTTGAAATGGATAACTTGGTGAATGAAGAAACTAATCTTGCTATGGCCG

CAGAGAATTCCTCATCGGTTGTAGAATTAAAGGTGAAACCAAAGACTAGAAGAT

GGAGTGATAAGAGAATGTGTCCTCCATGGAGGCTAAATTCACTAGAAACCATTG

TGCCTGAGAATCTTCCAAGGCCATCAGCTCGTCGGAGATGGGAGGCTACTGGTTA

TTCTAAGATTGATCCGGCTCCGGCTCCGGCAAGGAAAGTGTCAGTCAAAAGCATT

ATGATTATGGATAATTGCTTTACCATGTAA

SEQ ID NO: 34
MAITTSCCLNMNIPPPTSASSLPSSSSTTKPTAQASWFKNEKWRSQCVLGMACMIIGL

EMDNLVNEETNLAMAAENSSSVVELKVKPKTRRWSDKRMCPPWRLNSLETIVPENL

PRPSARRRWEATGYSKIDPAPAPARKVSVKSIMIMDNCFTM

>Solyc08g067630 (*Solanum lycopersicum*)
SEQ ID NO: 35
ATGGCTATTT CAACAAAGTT CTGCCTCAAT CTCTCCCCTC AACCTCCTCC

TACTTCTAAT TATAATAACT CAATTCCCCC ACCTTCAAAA AAAACTCAAC

TTTCTTGGTA AGTCTACTAC TACTTTTTAC ATTTTTTTTT ATTTATCATA

CTTTGCTTTT CGTTTTTGGA TGTTTGTCTA TGTTAAAAGT CGTGTGCATC

ATGTCCATAT CTATTCATCC ATTTCAATTT ATGTGATATT ATATATGTTC

ATTCATCTGT TTCATTTTAT ACGACATTAT ATATATATAT ATATATATAT

ATATACATTC AATTGTTTCA CTTTATATGA TTAAATTTTT TATTAATTTA

AACTACTATT TCATTTTTTT TTCGCAGGCA ACGAAAAGAA AAATCATGGA

AAAATCAATG TGTATTAGGA ATGGCATGTG TTGTAATTAT TGGATTAGAA

TTTGACGATT CAATTTTAGT TAATCAAGAA AGTACGATCG CGATCGCCGG

-continued

```
AGACATGCAA TTACAATATG TCGCCGGAAA ATCAATACAA AAATGGAGTG

AAAAAAGATC ATGCCCACCG TGGAACGTGA ACTCGTTAGA AACCATCGTG

CCGGAAAACT TACCGAGGCC GGTGACTCGC CGGAGATGGG AAAACGTTGA

TTATAATACT ACTACTCAAT CTGCACCTGA AGTAAAGTTG GTGACAAAAT

TTAGTAAAGG ATGTTTCACT ATGTGA
```

SEQ ID NO: 36
```
MAISTKFCLNLSPQPPPTSNYNNSIPPPSKKTQLSWQRKEKSWKNQCVLGMACVVIIG

LEFDDSILVNQESTIAIAGDMQLQYVAGKSIQKWSEKRSCPPWNVNSLETIVPENLPR

PVTRRRWENVDYNTTTQSAPEVKLVTKFSKGCFTM
```

>SB09G029300 (Sorghum bicolor-1)

SEQ ID NO: 37
```
ATGGCGGTCTCCTCCATCAGCTGCTCCCTTCGGCCTCCAGCTCCCGTCAGAGAAG

CTTCCGCTCGTCTGACGCCGCCGCAGCCGTCGCCACCAAAGACGACGGCCACGCC

GTGGGCGGACGGGCTGCGGCGGGCATGCGTGGCGGCGGCGGCAACCGCGGCGTG

CGTCGTGATCGGGACGGCGGGAGGTGGCGACGTGGTGGCGGCGTCGATGCCACG

CGACACCCCCGTTCTGGCTGTGGACGCGCGGCCGGCGGCGGCGGCGCCGCGGTG

GAGCGACCGCAGGGAGTGCCCGCCGTGGCGCGCTAACTCGCTGGAGAACATCGT

GCCGGAGAACCTGCCCCGCCCGTCGGCGCGCCGGAGGTTCAACACAGTCAAGCG

AGCGCCGCGGAAGGCCCCCGCGCTCGGGCGTCAAGCGGTGGCGCCGCCGTTCCT

GGCGCTGCGCTCCGGCGTGGACGACTGCTTCACCCTCTAG
```

SEQ ID NO: 38
```
MAVSSISCSLRPPAPVREASARLTPPQPSPPKTTATPWADGLRRACVAAAATAACVVI

GTAGGGDVVAASMPRDTPVLAVDARPAAAAPRWSDRRECPPWRANSLENIVPENLP

RPSARRRFNTVKRAPRKAPALGRQAVAPPFLALRSGVDDCFTL
```

>SB09G029310 (Sorghum bicolor-2)

SEQ ID NO: 39
```
ATGGCGGCTTCCTCCACCGCCACCACCATAATCAGCTGCTGCTGCTGCTGCCTCG

GGCCTCCCGCTCCGCCCAAAGAATCCTCTGCAGGCGCTCGCAGGCCGCAGGCGC

CGGCAGGCGTGTCAGTGTCGTCGCACGCGCTGCGCCGGGCGTGCGTGGCTGCCG

CGGCGTGCGCGATGGTGGGGATTTCGGGCGGCGGCGGCGGCGCCGACATGGCCC

TTGCGCTGGCGCGTGGCGGCGGCGCGTTCGCCTCCAGGACCGACGTCGTCGCCGT

GTCCGTGGGCGCCGCGCGCGCCAAGGCGCCGCCGCGGTGGAGCGACCGCAGGCA

GTGCCCGCCGTGGCGCGCCAACTCGCTGGAGAACATCGTGCCGGAGAACCTGCC

CCGCCCGTCCGCGCCCAGGAGGTTCGACAGCGTCTCGGCCTCGGCGGCCGCGCC

GGACTTGTCGGCGCCGCCTTCTTTCCTGGCGCTGCGACCCGGCACGGGCTGCTTC

TCACTCTGA
```

SEQ ID NO: 40
```
MAASSTATTIISCCCCCLGPPAPPKESSAGARRPQAPAGVSVSSHALRRACVAAAAC

AMVGISGGGGGADMALALARGGGAFASRTDVVAVSVGAARAKAPPRWSDRRQCP

PWRANSLENIVPENLPRPSARRRFDSVSASAAAPDLSAPPSFLALRPGTGCFSL
```

>TC09G013320 (Theobroma cacao)

SEQ ID NO: 41
```
ATGGCCATTTCAACTAGGTGCTGCCTCAATGTGTCCCCTCCAACTCCAACTCCTG

GCTTTGACATGTCTTCTTCTAACAAGAAGGCATCCCAAGTTGCATGGCCAAGGGA

TGATAAATGGAGGAAGCAATGTGTACTAGGGGTAACCTGCATCGTAATTGGATT
```

-continued

```
ACAAGTAGGTAATATAACTGACAACAGCGCCATTGCTGAGGAAGTCTCATCTGC

CACAGAGTCAAACTCGAAAGTAGCAAGATGGAGTGATAAAAGAGTGTGCCCTCC

ATGGAATGCAAATTCGCTGGAGACCATCGTGCCGGAGAATCTCCCACGACCATC

AGCTCATAGAAGATGGGAAGCTATTGGTTTCTCCAAGAATGCCCCGGCAGTCAG

AGTGAAAGTGACAACAAAAACAAGAACCAATTGCTTCTCCATGTAA
```

SEQ ID NO: 42

```
MAISTRCCLNVSPPTPTPGFDMSSSNKKASQVAWPRDDKWRKQCVLGVTCIVIGLQV

GNITDNSAIAEEVSSATESNSKVARWSDKRVCPPWNANSLETIVPENLPRPSAHRRW

EAIGFSKNAPAVRVKVTTKTRTNCFSM
```

>AZ916442 (Zea mays)

SEQ ID NO: 43

```
CCGTTTCACCGTTATATCTGCAGGGCGGACGGGCTGCGGCGGGCGTGCGTGGCG

GGCGCGGCGGCGTGCGTCGTGTTCGGGACGGCGGGAGGCGGCGGCGGCGGCGTG

GCCGCGTCGGCGCCGCCGCGCGACGCCTCCGTCGCGGCGGCCCCGCGGTGGAGC

GACCGCCGGGAGTGCCCGCCGTGGCGCGCCAACTCGCTGGAGAACGTCGTGCCG

GAGAACCTGCCCCGCCCGTCGGCGCGCCGGAGGTTCAGCACCGTCAAGCGGGCG

CCGCGGAAGGCCCCCGCGCTCGGGCCTCAGGCGGTGGCGCCGTCGCCGTTCCTG

GCGCTGCGATCCGGCATGGACGACTGCTTCACCCTC
```

SEQ ID NO: 44

```
PFHRYICRADGLRRACVAGAAACVVFGTAGGGGGVAASAPPRDASVAAAPRWSD

RRECPPWRANSLENVVPENLPRPSARRRFSTVKRAPRKAPALGPQAVAPSPFLALRS

GMDDCFTL
```

SEQ ID NO: 45

RxCxxWxxN

SEQ ID NO: 46

ExxxPENLPRxxxxxR

SEQ ID NO: 47

TTACACGTAATGAACTTCCAG

---

What is claimed is:

1. A plant exhibiting less stress-induced chloroplast degradation relative to a wild-type plant,
the plant exhibiting less stress-induced chloroplast degradation comprising mutation in a chloroplast vesiculation (CV) gene, wherein the CV gene encodes a CV protein comprising a consensus sequence as shown in SEQ ID NO: 45 and SEQ ID NO: 46, wherein the CV gene encodes a polypeptide comprising an amino acid sequence at least 90% identical to SEQ ID NO:2 or 30, wherein the plant is from a genus selected from the group consisting of Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Populus, Pyrus, Prunus, Raphanus, Secale, Senecio, Sinapis, Solanum, Sorghum, Theobroma, Trigonella, Triticum, Vitis, Vigna*, and *Zea*.

2. The plant of claim 1, wherein the CV gene encodes a polypeptide comprising an amino acid sequence at least 90% identical to SEQ ID NO: 30.

3. The plant of claim 1, wherein the CV gene comprises a sequence at least 90% identical to at least one of SEQ ID NOs: 1 or 29.

4. The plant of claim 1, wherein the CV gene encodes a polypeptide comprising an amino acid sequence at least 90% identical to SEQ ID NO:2.

5. A plant exhibiting less stress-induced chloroplast degradation relative to a wild-type plant,
the plant exhibiting less stress-induced chloroplast degradation comprising mutation in a chloroplast vesiculation (CV) gene, wherein the CV gene encodes a CV protein comprising a consensus sequence as shown in SEQ ID NO: 45 and SEQ ID NO: 46, wherein the CV gene encodes a polypeptide comprising an amino acid sequence at least 90% identical to SEQ ID NO: 30.

* * * * *